United States Patent [19]
Reed et al.

[11] Patent Number: 5,643,727
[45] Date of Patent: Jul. 1, 1997

[54] BCL-2 GENE INHIBITORY ELEMENT BINDING FACTOR

[75] Inventors: John C. Reed, Carlsbad; Masayoshi Harigai, San Diego, both of Calif.

[73] Assignee: La Jolla Cancer Research Foundation, La Jolla, Calif.

[21] Appl. No.: 390,858

[22] Filed: Feb. 16, 1995

[51] Int. Cl.$^6$ .............................. C12Q 1/68; C07H 21/04; A61K 38/16; C07K 14/47
[52] U.S. Cl. .............................. 435/6; 530/350; 530/358; 536/24.1
[58] Field of Search .............................. 435/6; 530/350, 530/358; 536/24.1

[56] References Cited

PUBLICATIONS

Lawrence, Henderson's Dictionary of Biological Terms, New York: John Wiley & Sons, p. 253.
Kamada et al. "A protein binding to CArG box motifs aand to single–stranded DNA functions as a transcriptional repressor", Gene 119: 229–236.
Miyashita, Toshiyuki et al. "Identification of p53–dependent Negative Response Element in the bcl–2 Gene." *Canc. Res.* 54:3131–3135 (1994a).
Miyashita, Toshiyuki et al., "Tumor Suppressor p53 is a Regulator of bcl–2 and bax Gene Expression in Vitro and In Vivo." *Oncogene* 9:1799–1805 (1994b).
Young, Robert L. and Korsmeyer, Stanley J. "A Negative Regulatory Element in the bcl–2 5'–Untranslated Region Inhibits Expression From an Upstream Promotor." *Mol. Cell Biol.* 13:3686–3697 (1993).

Khan, Farhat A., et al., "Cloning and Sequence Analysis of a Human Type A/B hnRNP Protein." *Fed. Eur. Biochem. Soc.* 290:159–161 (1991).

Dreyfuss, Gideon et al., "hnRNP Proteins and the Biogenesis of mRNA." *Ann. Rev. Biochem.* 62:289–321 (1993).

*Primary Examiner*—Jasemine C. Chambers
*Assistant Examiner*—Scott D. Priebe
*Attorney, Agent, or Firm*—Campbell & Flores LLP

[57] ABSTRACT

The present invention provides a bcl-2 gene inhibitory element (BIE), which can inhibit expression of a gene in position-dependent and orientation-dependent manner. The invention provides, for example, BIE-1, having the nucleotide sequence 5'-CAAGAATGCAA-3' (SEQ ID NO: 1), which acts in an orientation-dependent and position-dependent manner to down-regulate the expression of the bcl-2 gene. The invention also provides a BIE binding factor (BBF), which is a cellular factor that can bind to a BIE. The invention provides, for example, BBF-A, which binds to BIE-1, including a nucleic acid sequence (SEQ ID NO: 8) encoding a portion of the amino acid sequence (SEQ ID NO: 9) of BBF-A. The invention further provides an antibody that specifically binds BBF-A. The invention also provides screening assays for identifying agents that can increase or decrease the binding of a BBF to a BIE, modulate the expression of a nucleic acid molecule linked to a BIE or modulate apoptosis in a cell.

15 Claims, 10 Drawing Sheets

Negative Regulatory Element*

```
  GTAGACTGAT  ATTAACAATA  CTTACTAATA  ATAACGTGCC  TCATGAAATA
  AAGATCCGAA  AGGAATTGGA  ATAAAAATTT  CCTGCGTCTC  ATGCCAAGAG
5 GGAAACACCA  GAATCAAGTG  TTCCGCGTGA  TTGAAGACAC  CCCCTCGTCC
  AAGAATGCAA  AGCACATCCA  ATAAAATAGC  TGGATTATAA
```

\* - positions ⁻274 to ⁻84 of the human bcl-2 gene;
   (SEQ ID NO: 2)

FIG. I

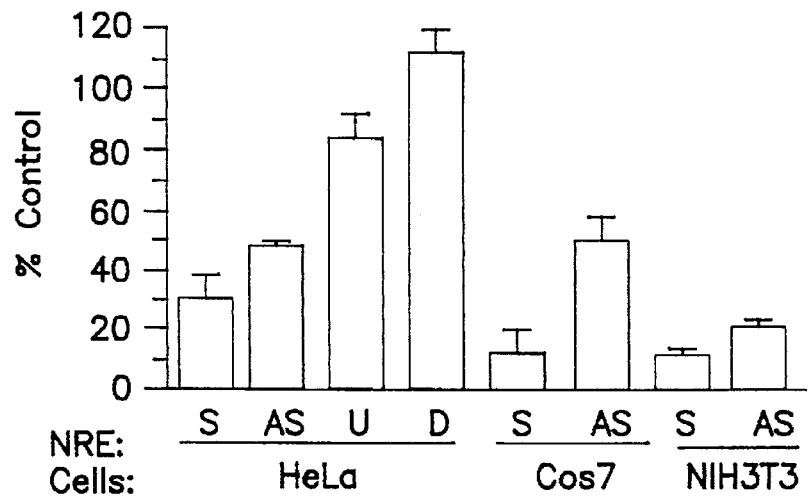
FIG. 2
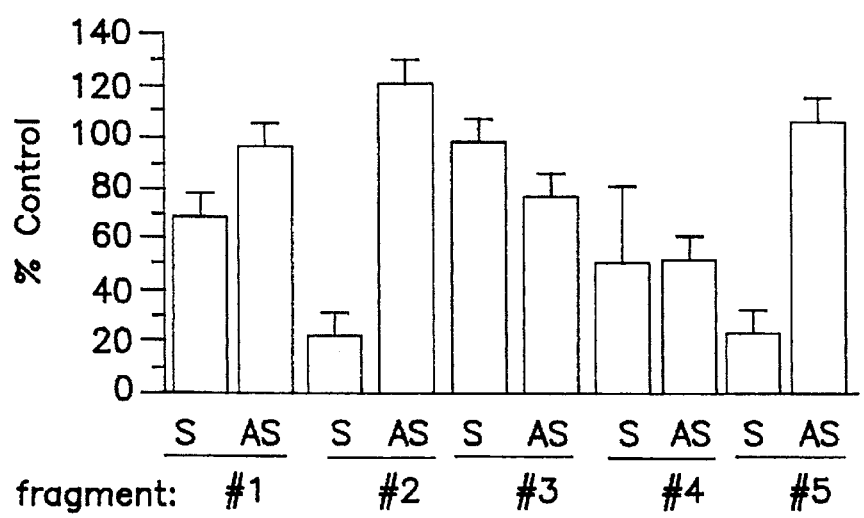
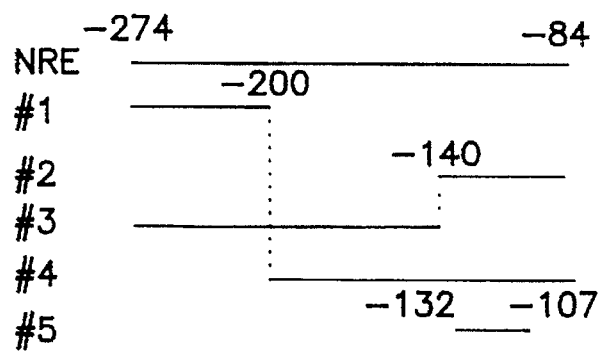
FIG. 3

```
             10         20         30         40         50
         1234567890 1234567890 1234567890 1234567890 1234567890
         GAATTCAAGCC GCGGGGCTGG GGGCGCGACC GCGGCGCCCC CGAGCGGGAA    50
          N  S  S  R   G  A  G   G  D  T   A  A  P  P  S  G  N

TCAGAACGGC GCCGAGGGCG ACCAGATCAA CGCCAGCAAG AACGAGGAGG   100
          Q  N  G   A  E  G  D   Q  I  N   A  S  K   N  E  E  D

ACGCGGGAAA AATGTTCGTT GGTGGCCTGA GCTGGGATAC TAGCAAAAAA   150
          A  G  K   M  F  V    G  G  L  S   W  D  T   S  K  K

GATTTAAAAG ACTATTTTAC TAAATTTGGA GAGGTCGTTG ACTGTACAAT   200
          D  L  K  D  Y  F  T   K  F  G   E  V  V  D   C  T  I

AAAAATGGAT CCCAACACTG GACGGTCAAG AGGGTTTGGG TTTATCCTGT   250
          K  M  D   P  N  T  G   R  S  R   G  F  G   F  I  L  F

TCAAAGATGC AGCCAGTGTG GAGAAGGTCC TAGACCAGAA GGAGCACAGG   300
          K  D  A   A  S  V   E  K  V  L   D  Q  K   E  H  R

CTGGATGGCC GTGTCATTGA CCCTAAAAAG GCCATGGCTA TGAAGAAGGA   350
          L  D  G  R   V  I  D   P  K  K   A  M  A  M   K  K  D

CCCGGTGAAG AAAATCTTCG TTGGGGGTCT GAATCCTGAA GCCACTGAGG   400
          P  V  K   K  I  F  V   G  G  L   N  P  E   A  T  E  E

AAAAGATCAG GGAGTACTTT GGCGAGTTTG GGGAGATTGA GGCCATTGAA   450
          K  I  R   E  Y  F   G  E  F  G   E  I  E   A  I  E

TTGCCAATGG ATCCAAAGTT GAACAAAAGA CGAGGTTTTG TGTTTATCAC   500
          L  P  M  D   P  K  L   N  K  R   R  G  F  V   F  I  T

CTTTAAAGAA GAAGAACCCG TGAAGAAGGT TCTGGAGAAA AAGTTCCATA   550
          F  K  E   E  E  P  V   K  K  V   L  E  K   K  F  H  T

CTGTCAGTGG AAGCAAGTGT GAGATCAAGG TGGCCCAGCC CAAAGAAGTC   600
          V  S  G   S  K  C   E  I  K  V   A  Q  P   K  E  V

TATCAGCAGC AGCAGTATGG CTCTGGGGGC CGTGGAAACC GCAACCGAGG   650
          Y  Q  Q  Q   Q  Y  G   S  G  G   R  G  N  R   N  R  G

GAA                                                     653
```

FIG. 7

| | | |
|---|---|---|
| Consensus | ATGAGGCCGT CCCCGAAGCG AGTCGCGGCC GGGGCTGGAC GRRYKCAMGC | 50 |
| hnRNP 200-1000 | ATGAGGCCGT CCCCGAAGCG AGTCGCGGCC GGGGCTGGAC GGGCGC-CGC | 49 |
| AYA 15 full length | ---------- ---------- ---------- ---------- -AATTCAAGC | 9 |
| Consensus | SGCGGGGCTG GRGGCGCGAC CGCSGCGCCC CCGAGCGGGA ATCAGAACGG | 100 |
| hnRNP 200-1000 | GGCGGGGCTG GAGGCGCGAC CGCCGCGCCC CCGAGCGGGA ATCAGAACGG | 99 |
| AYA 15 full length | CGCGGGGCTG GGGGCGCGAC CGCGGCGCCC CCGAGCGGGA ATCAGAACGG | 59 |
| Consensus | CGCCGAGGGC GACCAGATCA ACGCCAGCAA GAACGAGGAG GACGCGGGAA | 150 |
| hnRNP 200-1000 | CGCCGAGG-- GACCAGATCA ACGCCAGCAA GAACGAGGAG GACGCGGGAA | 147 |
| AYA 15 full length | CGCCGAGGGC GACCAGATCA ACGCCAGCAA GAACGAGGAG GACGCGGGAA | 109 |
| Consensus | AAATGTTCGT TGGTGGCCTG AGCTGGGATA CTAGCAAAAA AGATTTAAAA | 200 |
| hnRNP 200-1000 | AAATGTTCGT TGGTGGCCTG AGCTGGGATA CTAGCAAAAA AGATTTAAAA | 197 |
| AYA 15 full length | AAATGTTCGT TGGTGGCCTG AGCTGGGATA CTAGCAAAAA AGATTTAAAA | 159 |
| Consensus | GACTATTTTA CTAAATTTGG AGAGGTCGTT GACTGTACAA TAAAAATGGA | 250 |
| hnRNP 200-1000 | GACTATTTTA CTAAATTTGG AGAGGTCGTT GACTGTACAA TAAAAATGGA | 247 |
| AYA 15 full length | GACTATTTTA CTAAATTTGG AGAGGTCGTT GACTGTACAA TAAAAATGGA | 209 |
| Consensus | TCCCAACACT GGACGGTCAA GAGGGTTTGG GTTTATCCTG TTCAAAGATG | 300 |
| hnRNP 200-1000 | TCCCAACACT GGACGGTCAA GAGGGTTTGG GTTTATCCTG TTCAAAGATG | 297 |
| AYA 15 full length | TCCCAACACT GGACGGTCAA GAGGGTTTGG GTTTATCCTG TTCAAAGATG | 259 |
| Consensus | CAGCCAGTGT GGAGAAGGTC CTAGACCAGA AGGAGCACAG GCTGGATGGC | 350 |
| hnRNP 200-1000 | CAGCCAGTGT GGAGAAGGTC CTAGACCAGA AGGAGCACAG GCTGGATGGC | 347 |
| AYA 15 full length | CAGCCAGTGT GGAGAAGGTC CTAGACCAGA AGGAGCACAG GCTGGATGGC | 309 |
| Consensus | CGTGTCATTG ACCCTAAAAA GGCCATGGCT ATGAAGAAGG ACCCGGTSAA | 400 |
| hnRNP 200-1000 | CGTGTCATTG ACCCTAAAAA GGCCATGGCT ATGAAGAAGG ACCCGGTCAA | 397 |
| AYA 15 full length | CGTGTCATTG ACCCTAAAAA GGCCATGGCT ATGAAGAAGG ACCCGGTGAA | 359 |

FIG. 8A

```
Consensus              GAAAATCTTC GTTGGGGGTC TGAATCCTGA AAGTCCCACT GAGGAAAAGA    450 hnRNP 200-1000         GAAAATCTTC GTTGGGGGTC TGAATCCTGA AAGTCCCACT GAGGAAAAGA    447
AYA 15 full length     GAAAATCTTC GTTGGGGGTC TGAATCCTGA A-G--CCACT GAGGAAAAGA    406

Consensus              TCAGGGAGTA CTTTGGCGAG TTTGGGGAGA TTGAGGCCAT TGAATTGCCA    500 hnRNP 200-1000         TCAGGGAGTA CTTTGGCGAG TTTGGGGAGA TTGAGGCCAT TGAATTGCCA    497
AYA 15 full length     TCAGGGAGTA CTTTGGCGAG TTTGGGGAGA TTGAGGCCAT TGAATTGCCA    456

Consensus              ATGGATCCAA AGTTGAACAA AAGACGAGGT TTTGTGTTTA TCACCTTTAA    550 hnRNP 200-1000         ATGGATCCAA AGTTGAACAA AAGACGAGGT TTTGTGTTTA TCACCTTTAA    547
AYA 15 full length     ATGGATCCAA AGTTGAACAA AAGACGAGGT TTTGTGTTTA TCACCTTTAA    506

Consensus              AGAAGAAGAA CCCGTGAAGA AGGTTCTGGA GAAAAAGTTC CATACTGTCA    600 hnRNP 200-1000         AGAAGAAGAA CCCGTGAAGA AGGTTCTGGA GAAAAAGTTC CATACTGTCA    597
AYA 15 full length     AGAAGAAGAA CCCGTGAAGA AGGTTCTGGA GAAAAAGTTC CATACTGTCA    556

Consensus              GTGGAAGCAA GTGTGAGATC AAGGTGGCCC AGCCCAAAGA AGTCTATCAG    650 hnRNP 200-1000         GTGGAAGCAA GTGTGAGATC AAGGTGGCCC AGCCCAAAGA AGTCTATCAG    647
AYA 15 full length     GTGGAAGCAA GTGTGAGATC AAGGTGGCCC AGCCCAAAGA AGTCTATCAG    606

Consensus              CAGCAGCAGT ATGGCTCTGG GGGCCGTGGA AACCGCAACC GAGGGAACCG    700 hnRNP 200-1000         CAGCAGCAGT ATGGCTCTGG GGGCCGTGGA AACCGCAACC GAGGGAACCG    697
AYA 15 full length     CAGCAGCAGT ATGGCTCTGG GGGCCGTGGA AACCGCAACC GAGGGAA---    653

Consensus              AGGCAGCGGA GGTGGTGGTG GAGGTGGAGG TCAGGGTAGT ACAAACTACG    750 hnRNP 200-1000         AGGCAGCGGA GGTGGTGGTG GAGGTGGAGG TCAGGGTAGT ACAAACTACG    747
AYA 15 full length     ---------- ---------- ---------- ---------- ----------    653

Consensus              GCAAGAGCCA GCGACGTGGT GGCCATCAGA ATAACTACAA GCCATACTGA    800 hnRNP 200-1000         GCAAGAGCCA GCGACGTGGT GGCCATCAGA ATAACTACAA GCCATACTGA    797
AYA 15 full length     ---------- ---------- ---------- ---------- ----------    653

Consensus              GGC                                                       803 hnRNP 200-1000         GGC                                                       800
AYA 15 full length     ---                                                       653
```

FIG. 8B

```
Consensus              ..........  ..........  ......|SRG.  |G|..|GA|.|A|...  ...|P|.|P|....      50
BBF-A                  ----------  ----------  ----NSSRGA   |G|--|GA|I|A|---  --|AP|-|PSGNQ        18
hnRNP ORF   MSEAGEEQPM ETTGATENGH  EAVPEASRGR  |GWTGAAAGLE  ARP|P|R|P|RAGI                        50

Consensus   ..|A|..|DQINA  SKNEEDAGKM FVGGLSWDTS KKDLKDYFTK FGEVVDCTIK|                           100
BBF-A       NG|A|E|GDQINA  SKNEEDAGKM FVGGLSWDTS KKDLKDYFTK FGEVVDCTIK|                            68
hnRNP ORF   RT|A|PR|DQINA  SKNEEDAGKM FVGGLSWDTS KKDLKDYFTK FGEVVDCTIK|                           100

Consensus   |MDPNTGRSRG FGFILFKDAA SVEKVLDQKE HRLDGRVIDP KKAMAMKKDP|                              150
BBF-A       |MDPNTGRSRG FGFILFKDAA SVEKVLDQKE HRLDGRVIDP KKAMAMKKDP|                              118
hnRNP ORF   |MDPNTGRSRG FGFILFKDAA SVEKVLDQKE HRLDGRVIDP KKAMAMKKDP|                              150

Consensus   |VKKIFVGGLN PE|..|TEEKIR EYFGEFGEIE AIELPMDPKL NKRRGFVFIT                            200
BBF-A       |VKKIFVGGLN PE|-A|TEEKIR EYFGEFGEIE AIELPMDPKL NKRRGFVFIT                             167
hnRNP ORF   |VKKIFVGGLN PE|SP|TEEKIR EYFGEFGEIE AIELPMDPKL NKRRGFVFIT                             200

Consensus   |FKEEEPVKKV LEKKFHTVSG SKCEIKVAQP KEVYQQQQYG SGGRGNRNRG|                              250
BBF-A       |FKEEEPVKKV LEKKFHTVSG SKCEIKVAQP KEVYQQQQYG SGGRGNRNRG|                              217
hnRNP ORF   |FKEEEPVKKV LEKKFHTVSG SKCEIKVAQP KEVYQQQQYG SGGRGNRNRG|                              250

Consensus              ..........  ..........  ..........  ....                                  284
BBF-A                  ----------  ----------  ----------  ----                                  217
hnRNP ORF   NRGSGGGGGG GGQGSTNYGK  SQRRGGHQNN  YKPY                                              284
```

FIG. 9

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
( A ) LENGTH: 11 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:1:

```
CAAGAATGCA A                                                          11
```

( 2 ) INFORMATION FOR SEQ ID NO:2:

( i ) SEQUENCE CHARACTERISTICS:
( A ) LENGTH: 190 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:2:

```
GTAGACTGAT ATTAACAATA CTTACTAATA ATAACGTGCC TCATGAAATA AAGATCCGAA      60
AGGAATTGGA ATAAAAATTT CCTGCGTCTC ATGCCAAGAG GGAAACACCA GAATCAAGTG     120
TTCCGCGTGA TTGAAGACAC CCCCTCGTCC AAGAATGCAA AGCACATCCA ATAAAATAGC     180
TGGATTATAA                                                           190
```

( 2 ) INFORMATION FOR SEQ ID NO:3:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:3:

CTAGAATGCA A      11

( 2 ) INFORMATION FOR SEQ ID NO:4:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:4:

CAAGATTGCA A      11

( 2 ) INFORMATION FOR SEQ ID NO:5:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:5:

CAAGAATGCT A      11

( 2 ) INFORMATION FOR SEQ ID NO:6:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:6:

AAGAATGCAA      10

( 2 ) INFORMATION FOR SEQ ID NO:7:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:7:

CAAGAATGCA      10

( 2 ) INFORMATION FOR SEQ ID NO:8:

( i ) SEQUENCE CHARACTERISTICS:
    ( A ) LENGTH: 654 base pairs
    ( B ) TYPE: nucleic acid
    ( C ) STRANDEDNESS: double -continued (D) TOPOLOGY: linear (ii) MOLECULE TYPE: cDNA (ix) FEATURE:
    (A) NAME/KEY: CDS
    (B) LOCATION: 2..652

(xi) SEQUENCE DESCRIPTION: SEQ ID NO:8:

```
G AAT TCA AGC CGC GGG GCT GGG GGC GCG ACC GCG GCG CCC CCG AGC        46
  Asn Ser Ser Arg Gly Ala Gly Gly Ala Thr Ala Ala Pro Pro Ser
  1               5                   10                  15

GGG AAT CAG AAC GGC GCC GAG GGC GAC CAG ATC AAC GCC AGC AAG AAC      94
Gly Asn Gln Asn Gly Ala Glu Gly Asp Gln Ile Asn Ala Ser Lys Asn
                20                  25                  30

GAG GAG GAC GCG GGA AAA ATG TTC GTT GGT GGC CTG AGC TGG GAT ACT      142
Glu Glu Asp Ala Gly Lys Met Phe Val Gly Gly Leu Ser Trp Asp Thr
            35                  40                  45

AGC AAA AAA GAT TTA AAA GAC TAT TTT ACT AAA TTT GGA GAG GTC GTT      190
Ser Lys Lys Asp Leu Lys Asp Tyr Phe Thr Lys Phe Gly Glu Val Val
        50                  55                  60

GAC TGT ACA ATA AAA ATG GAT CCC AAC ACT GGA CGG TCA AGA GGG TTT      238
Asp Cys Thr Ile Lys Met Asp Pro Asn Thr Gly Arg Ser Arg Gly Phe
    65                  70                  75

GGG TTT ATC CTG TTC AAA GAT GCA GCC AGT GTG GAG AAG GTC CTA GAC      286
Gly Phe Ile Leu Phe Lys Asp Ala Ala Ser Val Glu Lys Val Leu Asp
80                  85                  90                  95

CAG AAG GAG CAC AGG CTG GAT GGC CGT GTC ATT GAC CCT AAA AAG GCC      334
Gln Lys Glu His Arg Leu Asp Gly Arg Val Ile Asp Pro Lys Lys Ala
                100                 105                 110

ATG GCT ATG AAG AAG GAC CCG GTG AAG AAA ATC TTC GTT GGG GGT CTG      382
Met Ala Met Lys Lys Asp Pro Val Lys Lys Ile Phe Val Gly Gly Leu
            115                 120                 125

AAT CCT GAA GCC ACT GAG GAA AAG ATC AGG GAG TAC TTT GGC GAG TTT      430
Asn Pro Glu Ala Thr Glu Glu Lys Ile Arg Glu Tyr Phe Gly Glu Phe
        130                 135                 140

GGG GAG ATT GAG GCC ATT GAA TTG CCA ATG GAT CCA AAG TTG AAC AAA      478
Gly Glu Ile Glu Ala Ile Glu Leu Pro Met Asp Pro Lys Leu Asn Lys
    145                 150                 155

AGA CGA GGT TTT GTG TTT ATC ACC TTT AAA GAA GAA GAA CCC GTG AAG      526
Arg Arg Gly Phe Val Phe Ile Thr Phe Lys Glu Glu Glu Pro Val Lys
160                 165                 170                 175

AAG GTT CTG GAG AAA AAG TTC CAT ACT GTC AGT GGA AGC AAG TGT GAG      574
Lys Val Leu Glu Lys Lys Phe His Thr Val Ser Gly Ser Lys Cys Glu
                180                 185                 190

ATC AAG GTG GCC CAG CCC AAA GAA GTC TAT CAG CAG CAG CAG TAT GGC      622
Ile Lys Val Ala Gln Pro Lys Glu Val Tyr Gln Gln Gln Gln Tyr Gly
            195                 200                 205

TCT GGG GGC CGT GGA AAC CGC AAC CGA GGG AA                           654
Ser Gly Gly Arg Gly Asn Arg Asn Arg Gly
        210                 215
```

(2) INFORMATION FOR SEQ ID NO:9:

(i) SEQUENCE CHARACTERISTICS:
        (A) LENGTH: 217 amino acids
        (B) TYPE: amino acid
        (D) TOPOLOGY: linear (ii) MOLECULE TYPE: protein (xi) SEQUENCE DESCRIPTION: SEQ ID NO:9:

```
Asn Ser Ser Arg Gly Ala Gly Gly Ala Thr Ala Ala Pro Pro Ser Gly
1               5                   10                  15
```

| | | | | | | | | | | | | | | |
|---|---|---|---|---|---|---|---|---|---|---|---|---|---|---|
| Asn | Gln | Asn | Gly | Ala | Glu | Gly | Asp | Gln | Ile | Asn | Ala | Ser | Lys | Asn | Glu |
| | | | 20 | | | | | 25 | | | | | 30 | | |
| Glu | Asp | Ala | Gly | Lys | Met | Phe | Val | Gly | Gly | Leu | Ser | Trp | Asp | Thr | Ser |
| | | | 35 | | | | 40 | | | | | 45 | | | |
| Lys | Lys | Asp | Leu | Lys | Asp | Tyr | Phe | Thr | Lys | Phe | Gly | Glu | Val | Val | Asp |
| | 50 | | | | | 55 | | | | | | 60 | | | |
| Cys | Thr | Ile | Lys | Met | Asp | Pro | Asn | Thr | Gly | Arg | Ser | Arg | Gly | Phe | Gly |
| 65 | | | | | 70 | | | | | 75 | | | | | 80 |
| Phe | Ile | Leu | Phe | Lys | Asp | Ala | Ala | Ser | Val | Glu | Lys | Val | Leu | Asp | Gln |
| | | | | 85 | | | | | 90 | | | | | 95 | |
| Lys | Glu | His | Arg | Leu | Asp | Gly | Arg | Val | Ile | Asp | Pro | Lys | Lys | Ala | Met |
| | | | 100 | | | | | 105 | | | | | 110 | | |
| Ala | Met | Lys | Lys | Asp | Pro | Val | Lys | Lys | Ile | Phe | Val | Gly | Gly | Leu | Asn |
| | | 115 | | | | | 120 | | | | | 125 | | | |
| Pro | Glu | Ala | Thr | Glu | Glu | Lys | Ile | Arg | Glu | Tyr | Phe | Gly | Glu | Phe | Gly |
| | 130 | | | | | 135 | | | | | 140 | | | | |
| Glu | Ile | Glu | Ala | Ile | Glu | Leu | Pro | Met | Asp | Pro | Lys | Leu | Asn | Lys | Arg |
| 145 | | | | | 150 | | | | | 155 | | | | | 160 |
| Arg | Gly | Phe | Val | Phe | Ile | Thr | Phe | Lys | Glu | Glu | Glu | Pro | Val | Lys | Lys |
| | | | | 165 | | | | | 170 | | | | | 175 | |
| Val | Leu | Glu | Lys | Lys | Phe | His | Thr | Val | Ser | Gly | Ser | Lys | Cys | Glu | Ile |
| | | | 180 | | | | | 185 | | | | | 190 | | |
| Lys | Val | Ala | Gln | Pro | Lys | Glu | Val | Tyr | Gln | Gln | Gln | Gln | Tyr | Gly | Ser |
| | | 195 | | | | | 200 | | | | | 205 | | | |
| Gly | Gly | Arg | Gly | Asn | Arg | Asn | Arg | Gly | | | | | | | |
| | 210 | | | | | 215 | | | | | | | | | |

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

GCGAAGCTTG TAGACTGATA TTAAC                                                   25

( 2 ) INFORMATION FOR SEQ ID NO:11:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

GCGAAGCTTA AAATTCCTG CATCTCAT                                           28

( 2 ) INFORMATION FOR SEQ ID NO:12:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GCGAAGCTTA AGACACCCCC TCGTCCAA                                              2 8

( 2 ) INFORMATION FOR SEQ ID NO:13:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:13:

GCGAAGCTTA TAATCCAGCT ATTTT                                                 2 5

( 2 ) INFORMATION FOR SEQ ID NO:14:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:14:

GCGAAGCTTT ATTCCAATTC CTTTCGGA                                              2 8

( 2 ) INFORMATION FOR SEQ ID NO:15:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:15:

GCGAAGCTTC AATCACGCGG AACACTTG                                              2 8

( 2 ) INFORMATION FOR SEQ ID NO:16:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:16:

AGCTGAATGC AAAGCACAT                                                        1 9

( 2 ) INFORMATION FOR SEQ ID NO:17:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:17:

AGCTATGTGC TTTGCATTC                                                        1 9

( 2 ) INFORMATION FOR SEQ ID NO:18:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

AGCTGCAAAG CACAT     15

( 2 ) INFORMATION FOR SEQ ID NO:19:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

AGCTATGTGT TTGC     14

( 2 ) INFORMATION FOR SEQ ID NO:20:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

AGCTAAAGCA CAT     13

( 2 ) INFORMATION FOR SEQ ID NO:21:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

AGCTATGTGC TTT     13

( 2 ) INFORMATION FOR SEQ ID NO:22:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

AGCTCAAGAA TG     12

( 2 ) INFORMATION FOR SEQ ID NO:23:

( i ) SEQUENCE CHARACTERISTICS:
        ( A ) LENGTH: 12 base pairs

-continued (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

AGCTCATTCT TG                                                                    12

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

GATCTCGCGG GGGCGAGGGG GATC                                                       24

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

CCACCCATGG CAAATTCCAT GGCA                                                       24

(2) INFORMATION FOR SEQ ID NO:26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

TCTAGACGGC AGGTCAGGTC CACC                                                       24

(2) INFORMATION FOR SEQ ID NO:27:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

AGCTCAAGAA TGCA                                                                  14

(2) INFORMATION FOR SEQ ID NO:28:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA ( x i ) SEQUENCE DESCRIPTION: SEQ ID NO:28:

AGCTTGCATT CTTG 14

( 2 ) INFORMATION FOR SEQ ID NO:29:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

AGCTCAAGAA TGCAAGCTAA GCTT 24

( 2 ) INFORMATION FOR SEQ ID NO:30:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

AAGCTTAGCT 10

( 2 ) INFORMATION FOR SEQ ID NO:31:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

TCTACAGAAT GCAAGCTCAG AATGCAAGCT CAGAATGCAA 40

( 2 ) INFORMATION FOR SEQ ID NO:32:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

TCGATTGCAT TCTTGAGCTT GCATTCTTGA GCTTGCATTC TTG 43

( 2 ) INFORMATION FOR SEQ ID NO:33:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

TCTACTGATT GCAAGCTCTG ATTGCAAGCT CTGATTGCAA 40

( 2 ) INFORMATION FOR SEQ ID NO:34:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

```
TCGATTGCAA TCATGAGCTT GCAATCATGA GCTTGCAATC ATG                    43
```

( 2 ) INFORMATION FOR SEQ ID NO:35:

( i ) SEQUENCE CHARACTERISTICS:
        ( A ) LENGTH: 800 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:35:

```
ATGAGGCCGT CCCCGAAGCG AGTCGCGGCC GGGGCTGGAC GGGCGCCGCG GCGGGGCTGG    60
AGGCGCGACC GCCGCGCCCC CGAGCGGGAA TCAGAACGGC GCCGAGGGAC CAGATCAACG   120
CCAGCAAGAA CGAGGAGGAC GCGGGAAAAA TGTTCGTTGG TGGCCTGAGC TGGGATACTA   180
GCAAAAAGA TTTAAAAGAC TATTTTACTA AATTTGGAGA GGTCGTTGAC TGTACAATAA    240
AAATGGATCC CAACACTGGA CGGTCAAGAG GGTTTGGGTT TATCCTGTTC AAAGATGCAG   300
CCAGTGTGGA GAAGGTCCTA GACCAGAAGG AGCACAGGCT GGATGGCCGT GTCATTGACC   360
CTAAAAAGGC CATGGCTATG AAGAAGGACC CGGTCAAGAA AATCTTCGTT GGGGGTCTGA   420
ATCCTGAAAG TCCCACTGAG GAAAAGATCA GGGAGTACTT TGGCGAGTTT GGGGAGATTG   480
AGGCCATTGA ATTGCCAATG GATCCAAAGT TGAACAAAAG ACGAGGTTTT GTGTTTATCA   540
CCTTTAAAGA AGAAGAACCC GTGAAGAAGG TTCTGGAGAA AAAGTTCCAT ACTGTCAGTG   600
GAAGCAAGTG TGAGATCAAG GTGGCCCAGC CCAAAGAAGT CTATCAGCAG CAGCAGTATG   660
GCTCTGGGGG CCGTGGAAAC CGCAACCGAG GGAACCGAGG CAGCGGAGGT GGTGGTGGAG   720
GTGGAGGTCA GGGTAGTACA AACTACGGCA AGAGCCAGCG ACGTGGTGGC CATCAGAATA   780
ACTACAAGCC ATACTGAGGC                                              800
```

( 2 ) INFORMATION FOR SEQ ID NO:36:

( i ) SEQUENCE CHARACTERISTICS:
        ( A ) LENGTH: 284 amino acids
        ( B ) TYPE: amino acid
        ( D ) TOPOLOGY: linear ( x i ) SEQUENCE DESCRIPTION: SEQ ID NO:36:

```
Met Ser Glu Ala Gly Glu Glu Gln Pro Met Glu Thr Thr Gly Ala Thr
 1               5                  10                  15
Glu Asn Gly His Glu Ala Val Pro Glu Ala Ser Arg Gly Arg Gly Trp
                20                  25                  30
Thr Gly Ala Ala Ala Gly Leu Glu Ala Arg Pro Pro Arg Pro Arg Ala
            35                  40                  45
Gly Ile Arg Thr Ala Pro Arg Asp Gln Ile Asn Ala Ser Lys Asn Glu
        50                  55                  60
Glu Asp Ala Gly Lys Met Phe Val Gly Gly Leu Ser Trp Asp Thr Ser
65                  70                  75                  80
```

```
Lys Lys Asp Leu Lys Asp Tyr Phe Thr Lys Phe Gly Glu Val Val Asp
             85                  90                  95
Cys Thr Ile Lys Met Asp Pro Asn Thr Gly Arg Ser Arg Gly Phe Gly
            100                 105                 110
Phe Ile Leu Phe Lys Asp Ala Ala Ser Val Glu Lys Val Leu Asp Gln
            115                 120                 125
Lys Glu His Arg Leu Asp Gly Arg Val Ile Asp Pro Lys Lys Ala Met
        130                 135                 140
Ala Met Lys Lys Asp Pro Val Lys Lys Ile Phe Val Gly Gly Leu Asn
145                 150                 155                 160
Pro Glu Ser Pro Thr Glu Glu Lys Ile Arg Glu Tyr Phe Gly Glu Phe
                165                 170                 175
Gly Glu Ile Glu Ala Ile Glu Leu Pro Met Asp Pro Lys Leu Asn Lys
            180                 185                 190
Arg Arg Gly Phe Val Phe Ile Thr Phe Lys Glu Glu Pro Val Lys
        195                 200                 205
Lys Val Leu Glu Lys Lys Phe His Thr Val Ser Gly Ser Lys Cys Glu
        210                 215                 220
Ile Lys Val Ala Gln Pro Lys Glu Val Tyr Gln Gln Gln Gln Tyr Gly
225                 230                 235                 240
Ser Gly Gly Arg Gly Asn Arg Asn Arg Gly Asn Arg Gly Ser Gly Gly
                245                 250                 255
Gly Gly Gly Gly Gly Gly Gln Gly Ser Thr Asn Tyr Gly Lys Ser Gln
            260                 265                 270
Arg Arg Gly Gly His Gln Asn Asn Tyr Lys Pro Tyr
        275                 280
```

( 2 ) INFORMATION FOR SEQ ID NO:37:

( i ) SEQUENCE CHARACTERISTICS:
        ( A ) LENGTH: 803 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

```
ATGAGGCCGT CCCCGAAGCG AGTCGCGGCC GGGGCTGGAC GRR YKCAMGC SGCGGGGCTG      60
GRGGCGCGAC CGCSGCGCCC CCGAGCGGGA ATCAGAACGG CGCCGAGGGC GACCAGATCA     120
ACGCCAGCAA GAACGAGGAG GACGCGGGAA AAATGTTCGT TGGTGGCCTG AGCTGGGATA     180
CTAGCAAAAA AGATTTAAAA GACTATTTTA CTAAATTTGG AGAGGTCGTT GACTGTACAA     240
TAAAAATGGA TCCCAACACT GGACGGTCAA GAGGGTTTGG GTTTATCCTG TTCAAAGATG     300
CAGCCAGTGT GGAGAAGGTC CTAGACCAGA AGGAGCACAG GCTGGATGGC CGTGTCATTG     360
ACCCTAAAAA GGCCATGGCT ATGAAGAAGG ACCCGGTSAA GAAAATCTTC GTTGGGGGTC     420
TGAATCCTGA AAGTCCCACT GAGGAAAAGA TCAGGGAGTA CTTTGGCGAG TTTGGGGAGA     480
TTGAGGCCAT TGAATTGCCA ATGGATCCAA AGTTGAACAA AAGACGAGGT TTTGTGTTTA     540
TCACCTTTAA AGAAGAAGAA CCCGTGAAGA AGGTTCTGGA GAAAAAGTTC CATACTGTCA     600
GTGGAAGCAA GTGTGAGATC AAGGTGGCCC AGCCCAAAGA AGTCTATCAG CAGCAGCAGT     660
ATGGCTCTGG GGGCCGTGGA AACCGCAACC GAGGGAACCG AGGCAGCGGA GGTGGTGGTG     720
GAGGTGGAGG TCAGGGTAGT ACAAACTACG GCAAGAGCCA GCGACGTGGT GGCCATCAGA     780
ATAACTACAA GCCATACTGA GGC                                             803
```

( 2 ) INFORMATION FOR SEQ ID NO:38:

( i ) SEQUENCE CHARACTERISTICS:
    ( A ) LENGTH: 107 amino acids
    ( B ) TYPE: amino acid
    ( D ) TOPOLOGY: linear ( x i ) SEQUENCE DESCRIPTION: SEQ ID NO:38:

```
Asp Gln Ile Asn Ala Ser Lys Asn Glu Glu Asp Ala Gly Lys Met Phe
 1               5                  10                  15
Val Gly Gly Leu Ser Trp Asp Thr Ser Lys Lys Asp Leu Lys Asp Tyr
            20                  25                  30
Phe Thr Lys Phe Gly Glu Val Val Asp Cys Thr Ile Lys Met Asp Pro
        35                  40                  45
Asn Thr Gly Arg Ser Arg Gly Phe Gly Phe Ile Leu Phe Lys Asp Ala
    50                  55                  60
Ala Ser Val Glu Lys Val Leu Asp Gln Lys Glu His Arg Leu Asp Gly
65                  70                  75                  80
Arg Val Ile Asp Pro Lys Lys Ala Met Ala Met Lys Lys Asp Pro Val
                85                  90                  95
Lys Lys Ile Phe Val Gly Gly Leu Asn Pro Glu
            100                 105
```

( 2 ) INFORMATION FOR SEQ ID NO:39:

( i ) SEQUENCE CHARACTERISTICS:
    ( A ) LENGTH: 86 amino acids
    ( B ) TYPE: amino acid
    ( D ) TOPOLOGY: linear ( x i ) SEQUENCE DESCRIPTION: SEQ ID NO:39:

```
Thr Glu Glu Lys Ile Arg Glu Tyr Phe Gly Glu Phe Gly Glu Ile Glu
 1               5                  10                  15
Ala Ile Glu Leu Pro Met Asp Pro Lys Leu Asn Lys Arg Arg Gly Phe
            20                  25                  30
Val Phe Ile Thr Phe Lys Glu Glu Glu Pro Val Lys Lys Val Leu Glu
        35                  40                  45
Lys Lys Phe His Thr Val Ser Gly Ser Lys Cys Glu Ile Lys Val Ala
    50                  55                  60
Gln Pro Lys Glu Val Tyr Gln Gln Gln Gln Tyr Gly Ser Gly Gly Arg
65                  70                  75                  80
Gly Asn Arg Asn Arg Gly
                85
```

BCL-2 GENE INHIBITORY ELEMENT BINDING FACTOR

BACKGROUND OF THE INVENTION

1. Field of the Invention

This invention relates generally to the fields of molecular biology and molecular medicine and more specifically to a novel gene regulatory element and to a cellular factor that binds to the regulatory element.

2. Background Information

Programmed cell death is important for maintaining a steady-state number of cells in a tissue such as skin or intestine that undergoes continual cell renewal. The term "apoptosis" is used to describe a series of morphological events that occurs during the programmed death of cell.

The progression of apoptosis in a cell is regulated by various cellular factors. Apoptosis can be induced by cellular, hormonal or external stimuli to remove unwanted cells from the body. For example, tumor cells and virus-infected cells can be killed via apoptosis by cytolytic T cells following target recognition. Apoptosis also is involved in cell death induced during treatment of a cancer patient by chemotherapy or X-irradiation.

Aberrant regulation of apoptosis can cause a variety of disease states and is associated with various pathological conditions. For example, the death of neurons that occurs in diseases such as Alzheimer's dementia and Parkinson's disease have the hallmarks of apoptosis. Viral infections also can affect the progression of apoptosis in a cell. For example, in the T cell death that is induced by the human immunodeficiency virus, viral infection induces apoptosis. In contrast, during persistent, latent infection of herpes simplex virus, viral infection can inhibit apoptosis through the expression of gene products that block apoptosis.

The bcl-2 gene, which was discovered due to its involvement in a chromosome translocation commonly found in non-Hodgkin's lymphoma, encodes the Bcl-2 protein, which is involved in regulating apoptosis. Low levels of Bcl-2 are associated with increased levels of apoptosis, whereas high levels of Bcl-2 can block cell death. For example, Bcl-2 expression is associated with the survival of long-lived cells such as "memory" lymphocytes, neurons in the brain and in peripheral nerves that control muscle and organ functions and stem cells in the bone marrow, skin and gastrointestinal tract.

In the United States, high levels of Bcl-2 are expected to be present in approximately 50,000 new cases of lymphoma and leukemia each year. High levels of Bcl-2 also are present in essentially all cases of drug-resistant prostate cancer (150,000 cases per year) and colorectal carcinoma (110,000 cases per year), about 80% of nasopharyngeal carcinoma cases and about 70% of breast cancer cases (100,000 cases per year) in the United States. It is likely that inappropriate activation of the bcl-2 gene and resultant high levels of Bcl-2 expression in tumor cells contribute to expansion of a tumor cell population by decreasing the rate of cell death.

The association of proteins such as Bcl-2 with apoptosis in normal cells and in cells associated with various pathological conditions suggests that manipulation of the expression of these proteins can be useful to effect cell death. However, a means for regulating the expression of the genes encoding these proteins has not been available. Thus, a need exists to identify the gene regulatory elements for proteins involved in apoptosis in order to modulate the regulation of programmed cell death. The present invention satisfies this need and provides related advantages as well.

SUMMARY OF THE INVENTION

The present invention relates to a nucleotide sequence that reduces or inhibits the expression of a gene such as bcl-2, which encodes a protein involved in controlling cell death. The invention provides a bcl-2 gene inhibitory element (BIE), designated BIE-1, that has the nucleotide sequence 5'-CAAGAATGCAA-3' (SEQ ID NO: 1) and acts in an orientation-dependent and position-dependent manner to down-regulate the expression of a gene.

The invention also relates to a cellular factor that can bind to a BIE. For example, the invention provides a BIE binding factor (BBF) such as a polypeptide portion of BBF-A, which has the amino acid sequence shown in FIG. 7 (SEQ ID NO: 9) and can bind to BIE-1. In addition, the invention provides a nucleic acid sequence (SEQ ID NO: 8) encoding the portion of BBF-A shown as SEQ ID NO: 9. The invention also provides an antibody that specifically binds BBF-A. The binding of a BBF to a BIE can regulate the level of expression of a nucleic acid molecule linked to the BIE. For example, binding of BBF-A to BIE-1 in a cell can regulate the level of bcl-2 gene expression, which can modulate the apoptosis in a cell.

The invention further relates to methods for identifying agents that can alter the association of a BBF and a BIE. An agent that can increase or decrease, for example, the binding of BBF-A to BIE-1 in a cell, can alter the expression of Bcl-2, which is involved in apoptosis, and, therefore, can modulate apoptosis in a cell.

BRIEF DESCRIPTION OF THE DRAWINGS

FIG. 1 shows the nucleotide sequence for the bcl-2 gene negative regulatory element (NRE; SEQ ID NO: 2). The NRE is present in the 5'-untranslated region (5'-UTR) at positions ⁻274 to ⁻84 of the human bcl-2 gene. The 11 base pair (bp) bcl-2 gene inhibitory element (BIE-1; SEQ ID NO: 1) located at positions ⁻124 to ⁻114 is underlined.

FIG. 2 demonstrates the effect of the NRE on expression of a chloramphenicol acetyltransferase (CAT) reporter gene from the SV40 promotor. A DNA fragment corresponding to the entire bcl-2 NRE (see FIG. 1; SEQ ID NO: 2) was subcloned in the sense (S) or antisense (AS) orientation between the SV40 promotor and the CAT gene or was subcloned upstream (U) or downstream (D) of the SV40-CAT transcription unit in the sense orientation. The various constructs were cotransfected with pCMV-β-gal into HeLa, Cos7 or NIH 3T3 cells and CAT assays were performed. Assay results were normalized relative to β-galactosidase (β-gal) activity. Data represent mean±standard deviation (SD) for 3 separate experiments (n=3) and are expressed as the percent CAT activity relative to the CAT activity in cells transfected with pUCSV3CAT lacking an NRE (100%).

FIG. 3 demonstrates that positions ⁻140 to ⁻84 and positions ⁻132 to ⁻107 of the NRE located in the 5'-UTR of the bcl-2 gene contain an orientation-dependent inhibitory element. Various fragments of the NRE as shown at bottom of the figure were subcloned between the SV40 promotor and the CAT gene in pUCSV3CAT in either the sense (S) or antisense (AS) orientation. Constructs were transfected into HeLa cells and CAT activity was measured 2 days later. Data are expressed as the percent CAT activity relative to the CAT activity in cells transfected with pUCSV3CAT lacking any bcl-2 sequences and normalized relative to β-gal (mean±SD; n=4).

FIG. 4, panels A to D, shows that the 11 bp BIE-1 sequence (SEQ ID NO: 1) located at positions ⁻124 to ⁻114 of the bcl-2 gene inhibits the expression of an upstream heterologous or homologous promotor. CAT constructs were transfected into either HeLa cells (FIGS. 4A to 4C) or TSU-prl cells (FIG. 4D). Data are expressed as a percentage relative to results obtained for pUCSV3CAT, pCEP-CAT and P1-CAT plasmids lacking bcl-2 sequences and are normalized relative to β-gal (mean±SD; n=3).

Figure 4A:
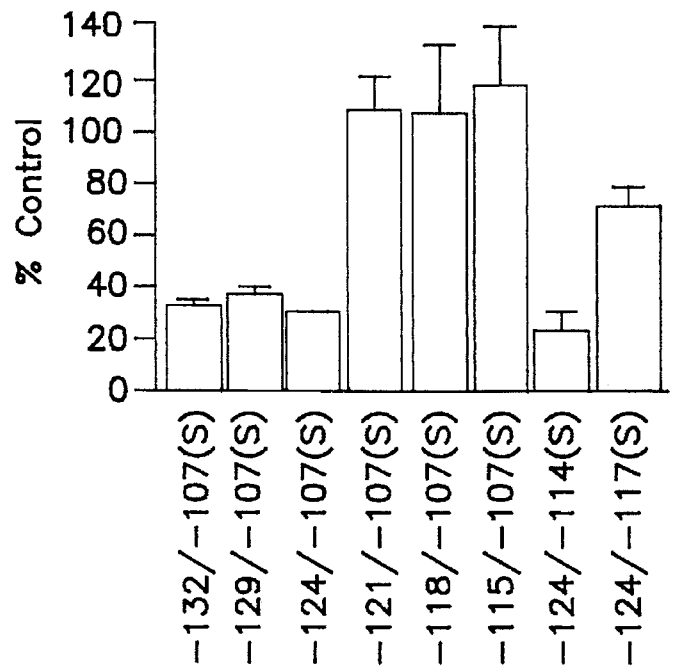

FIG. 4A shows the effect of several truncation mutants of the ⁻132 to ⁻107 bcl-2 BIE sequence, which were subcloned into pUCSV3CAT in the sense (S) orientation.

Figure 4B:
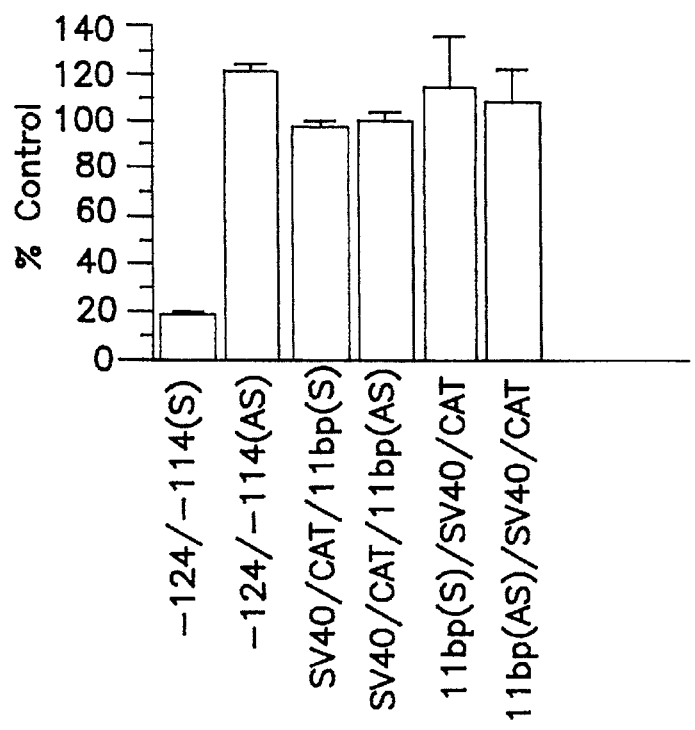

FIG. 4B shows the effect of the ⁻124 to ⁻114 BIE-1 sequence (SEQ ID NO: 1), which was subcloned into pUCSV3CAT between the SV40 promoter and CAT reporter gene in sense (S) or antisense (AS) orientation or downstream (SV40/CAT/11bp) or upstream (11bp/SV40/CAT) of CAT in the sense (S) or antisense (AS) orientation.

Figure 4C:
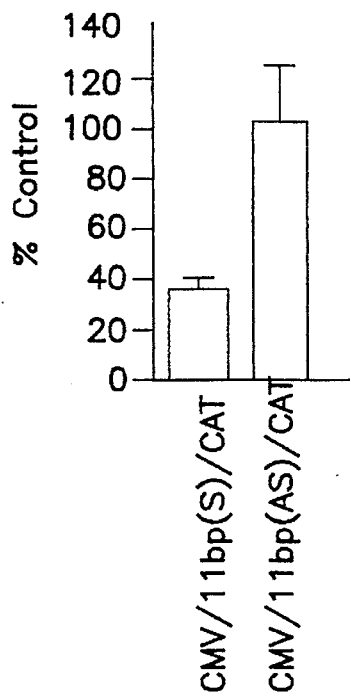

FIG. 4C shows the effect of the BIE-1 sequence (SEQ ID NO: 1), which was subcloned into pCEP-CAT between the CMV promoter and the CAT reporter gene.

Figure 4D:
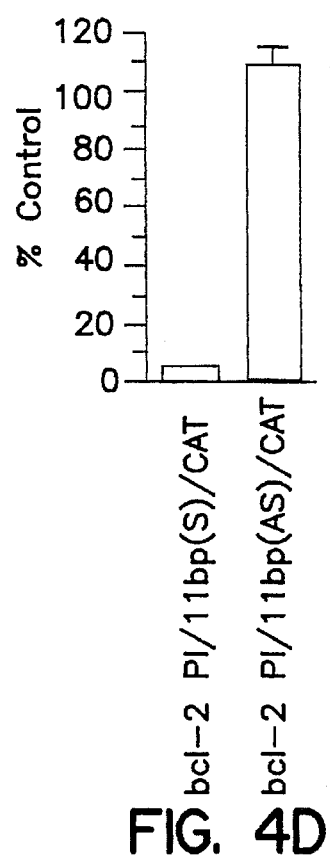

FIG. 4D shows the effect of BIE-1 (SEQ ID NO: 1), which was subcloned into P1-CAT between the bcl-2 P1 promotor and the CAT reporter gene.

Figure 5:
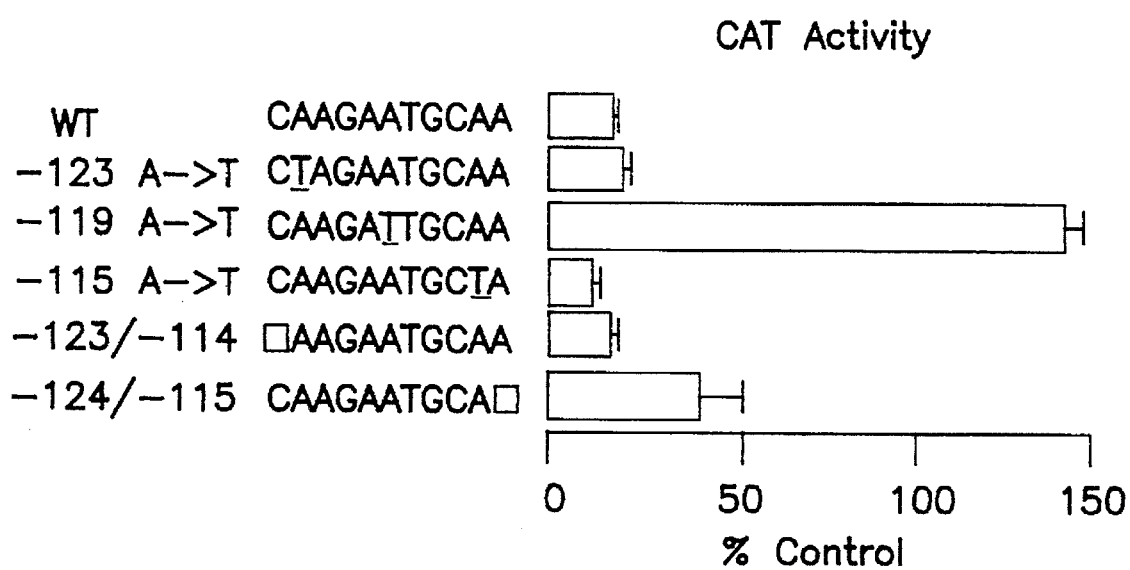

FIG. 5 shows the effect of point mutations on the inhibitory activity of BIE-1. The wild-type BIE-1 sequence (WT; SEQ ID NO: 1) or oligonucleotides containing various mutations of the wild-type BIE-1 (SEQ ID NOS: 3–7) were synthesized and subcloned in the sense orientation between the SV40 promoter and the CAT gene in pUCSV3CAT. The constructs were transfected into HeLa cells and CAT assays were performed. Data are expressed as a percentage relative to results obtained for cells transfected with pUCSV3CAT lacking wild type or mutant oligonucleotides (100%) after normalization for β-gal (mean±SD; n=3). Underlined letters (T) indicate point mutations; open squares indicate deletions.

Figure 6:
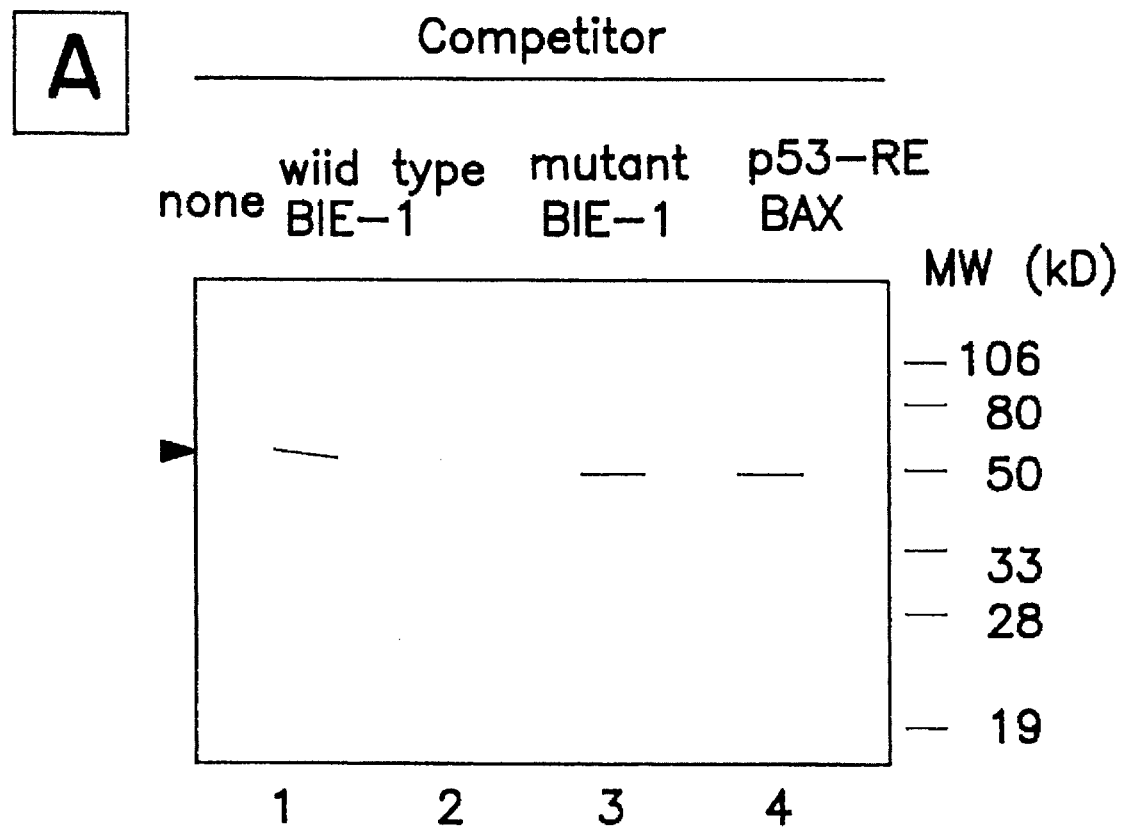

FIG. 6 demonstrates that a protein having an apparent molecular mass of about 47 kiloDaltons (kDa) that is present in a HeLa cell extract specifically binds a $^{32}$P-labelled BIE-1. Binding reactions were performed in the absence (lane 1; none) or presence (lanes 2–4) of various nucleic acid competitors as follows: lane 2, "wild type BIE-1" sequence; lane 3, a "mutant BIE-1" sequence containing 2 mismatches in the 11 bp BIE-1; lane 4, an irrelevant "p53-RE BAX" regulatory element. MW (kD) indicates the migration position of molecular weight markers, as shown.

FIG. 7 shows the partial cDNA sequence (SEQ ID NO: 8) and deduced amino acid sequence (SEQ ID NO: 9) for a portion of a BIE-1 binding factor obtained by screening a HeLa cell-derived cDNA expression library with a probe containing tandem copies of BIE-1. Numbers indicate nucleotide position relative to the first deduced amino acid residue.

FIG. 8 shows that the nucleotide sequence encoding BBF-A ("AYA 15 full length"; SEQ ID NO: 8) is highly homologous to heteronuclear ribonucleoprotein, hnRNP A/B (SEQ ID NO: 35). "hnRNP 200–1000" indicates nucleotides 200 to 1000 of hnRNP A/B. Numbers on right indicate nucleotide position. Identical nucleotides are boxed. "-" indicates space inserted to maintain sequence alignment. "Consensus" sequence also is shown (SEQ ID NO: 37). In the consensus sequence, "R" means a purine, "Y" means a pyrimidine, "K" means guanine or thymine, "M" means adenine or cytosine and "S" means cytosine or guanine.

FIG. 9 shows that the amino acid sequence of BBF-A ("BBF-A"; SEQ ID NO: 9) is highly homologous to the amino acid sequence for heteronuclear ribonucleoprotein, hnRNP A/B (SEQ ID NO: 36). "hnRNP ORF" indicates the open reading frame of hnRNP A/B. Numbers on right indicate amino acid position. Identical amino acids are boxed. "-" indicates space inserted to maintain sequence alignment. "Consensus" sequence also is shown (SEQ ID NOS: 38 and 39). "." indicates positions where no consensus could be identified.

DETAILED DESCRIPTION OF THE INVENTION

The present invention provides a substantially purified bcl-2 inhibitory element (BIE), which is a nucleotide sequence that corresponds to a portion of the NRE located in the 5'-untranslated region (5'-UTR) of the bcl-2 gene (see FIG. 1; SEQ ID NO: 2). As disclosed herein, a BIE inhibits the expression of a gene from a homologous or heterologous promotor in a position-dependent and orientation-dependent manner.

When used in referring to a BIE or a BBF, the term "substantially purified" means a BIE or a BBF that is in a form that is relatively free from contaminating lipids, proteins, nucleic acids or other cellular material normally associated with a BIE or a BBF in a cell. A substantially purified BIE can be obtained, for example, by recombinant DNA methods as described herein (see, also, Sambrook et al., *Molecular Cloning: A laboratory manual* (Cold Spring Harbor Laboratory Press 1989), which is incorporated herein by reference) or can be chemically synthesized.

A BIE of the invention is exemplified by bcl-2 gene inhibitory element-1 (BIE-1) having the nucleotide sequence 5'-CAAGAATGCAA-3' (SEQ ID NO: 1), which corresponds to positions ⁻124 to ⁻114 in the 5'-UTR of the human bcl-2 gene. The nucleotide sequence for BIE-1 is completely conserved among the bcl-2 genes of humans, mice and rats and has 88% identity with the corresponding sequence in the chicken bcl-2 gene. A BIE of the invention is further exemplified by nucleotide sequences that correspond to BIE-1, including the nucleotide sequences shown SEQ ID NOS: 3, 5, 6 and 7 in FIG. 5.

A BIE reduces or inhibits the expression of a nucleic acid molecule such as a gene from a homologous or heterologous promotor in a position-dependent and orientation-dependent manner. When used in reference to a BIE, the term "position-dependent" means that a BIE can reduce or inhibit gene expression only when positioned between a promoter and the translation start site of a gene and the term "orientation-dependent" means that a BIE can reduce or inhibit gene expression only when present in the sense orientation relative to the orientation of a corresponding sequence in the 5'-UTR of the human bcl-2 gene.

As used herein, the term "bcl-2 inhibitory element" or "BIE" means a nucleotide sequence that corresponds to a portion of the NRE (SEQ ID NO: 2) present in the 5'-UTR of the human bcl-2 gene, including a nucleotide sequence that corresponds to position ⁻124 to ⁻114 (SEQ ID NO: 1) of the bcl-2 gene, and that can reduce or inhibit the expression of a nucleic acid molecule to which it is linked. Various regions of the 5'-UTR of the bcl-2 gene have BIE activity, including, for example, sequences corresponding to positions ⁻124 to ⁻114 (BIE-1; SEQ ID NO: 1), ⁻140 to ⁻84 and ⁻132 to ⁻107 of the 5'-UTR of the bcl-2 gene (see FIG. 1).

BIE activity was identified by detecting decreased expression of a reporter gene from homologous and heterologous promotors (see Example I.B.). However, a nucleotide sequence having a sequence corresponding to a BIE is inactive when cloned in the reverse (antisense) orientation or when positioned upstream of the promotor or downstream of the CAT reporter gene (see FIG. 4). Thus, a BIE is characterized not only by its nucleotide sequence, which corresponds to a portion of the NRE located in the 5'-UTR of the human bcl-2 gene, but also by the requirement that, in order to confer BIE activity, it is located in the sense orientation (orientation dependent) between a promotor and a nucleic acid molecule linked to the promotor (position-dependent) to confer inhibitory activity. Since the presence of BIE-1 in the 5'-UTR of CAT mRNA had only minimal effect on mRNA translation efficiency or mRNA stability (see Example II.A.), the inhibitory activity of BIE-1 likely occurs at the level of gene transcription.

A BIE is characterized, in part, by its nucleotide sequence, which corresponds to a portion of the NRE located in the 5'-UTR of the human bcl-2 gene. When used in reference to a BIE, the term "corresponds" means the nucleotide sequence of a BIE is the same as or substantially the same as a portion of the sequence shown in FIG. 1 (SEQ ID NO: 2), provided there is included therein a sequence corresponding to positions ⁻124 to ⁻114 (SEQ ID NO: 1).

A BIE having a nucleotide sequence that is substantially the same as a portion of the sequence shown in FIG. 1 can contain one or a few nucleotide changes as compared to the sequence shown in FIG. 1 (SEQ ID NO: 1), provided the nucleotide sequence retains BIE activity (see, for example, FIG. 5, SEQ ID NOS: 3 and 5 to 7). A BIE having a nucleotide sequence that corresponds to a portion of the NRE located in the 5'-UTR of the human bcl-2 gene can be identified using, for example, site-directed mutagenesis and a functional assay as disclosed herein (see Example I).

A BIE such as BIE-1 can be used as a probe to screen a genomic or cDNA library to identify novel nucleotide sequences that can hybridize to the BIE under relatively stringent conditions. Where such a novel nucleotide sequence is demonstrated to have BIE activity, the novel nucleotide sequence, which corresponds to a portion of the NRE located in the 5'-UTR of the human bcl-2 gene, is a BIE as disclosed herein. As used herein, the term "BIE activity" refers to the ability of a BIE as disclosed herein to reduce or inhibit the expression of a nucleic acid molecule to which it is linked in a position-dependent and orientation-dependent manner. A nucleotide sequence that hybridizes to a BIE also can be useful for identifying genes that are linked to the BIE and, therefore, are regulated due, at least in part, to BIE activity.

When used in reference to BIE activity, the phrase "reduce or inhibit" means that the activity of a BIE is to decrease the level of transcription of a nucleotide sequence to which the BIE is linked. The terms "reduce" and "inhibit" have their common meanings and are used together here to avoid any ambiguity as to the extent to which the level of transcription is decreased. It is recognized, for example, that the level of gene transcription can be decreased below a level that is detectable using a particular assay such as a CAT assay. In such a case, one would be unable to determine whether the level of transcription was reduced to an undetectable level or inhibited such that no transcription was occurring. The use of these terms together precludes the need to distinguish these events.

A nucleic acid molecule linked to a BIE can be a naturally occurring molecule such as the bcl-2 gene or can be a recombinant nucleic acid molecule containing a BIE that is operably linked to a second nucleotide sequence, such that expression of the second nucleotide sequence is regulated, at least in part, due to the BIE. The second nucleotide sequence can be expressed as a transcript such as an antisense RNA sequence or a ribozyme, which can produce a desirable effect in a cell, or can encode a gene product, which can be, for example, a reporter gene product, a toxin, a growth factor or other desirable gene product. BIE activity can be detected using the methods disclosed herein or otherwise known in the art.

A BIE can be useful as a hybridization probe to identify other BIE sequences in a cell and, by association, genes that are linked to and can be regulated by the BIE. A BIE useful for hybridization should be at least ten nucleotides in length and can be prepared, for example, by restriction endonuclease digestion of a nucleic acid sequence containing the NRE located in the 5'-UTR of a bcl-2 gene such as the human bcl-2 gene (SEQ ID NO: 2), by PCR amplification of a portion of the nucleic acid molecule shown in FIG. 1 (SEQ ID NO: 2) or a homologous nucleic acid molecule encoding, for example, a rat, mouse or chicken bcl-2 gene, or by chemical synthesis, provided the sequence used for hybridization contains a nucleotide sequence corresponding to positions ⁻124 to ⁻114 of the bcl-2 gene. It should be recognized that a nucleotide sequence that is complementary to the sequences disclosed herein are considered to be encompassed with the disclosed sequences.

Relatively stringent hybridization conditions can be determined empirically or can be estimated based, for example, on the relative GC:AT content of the hybridizing nucleotide sequence and the target sequence, the length of the hybridizing nucleotide sequence and the number, if any, of mismatches between the hybridizing nucleotide sequence and the target sequence (see, for example, Sambrook et al., supra, 1989). If desired, a hybridizing nucleotide sequence can be detectably labelled and used as a probe or can be used as a primer for PCR. Methods for detectably labelling a nucleotide sequence are well known in the art (see, for example, Sambrook et al., supra, 1989); see, also, Ausubel et al., *Current Protocols in Molecular Biology* (Greene Publ., NY 1994), which is incorporated herein by reference).

The bcl-2 gene was first discovered by virtue of its involvement in t(14;18) chromosomal translocations commonly found in non-Hodgkin's lymphomas. In these translocations, the bcl-2 gene is translocated from its normal location on chromosome 18 into juxtaposition with enhancer elements present in the immunoglobulin heavy chain (IgH) locus on chromosome 14. Proximity of bcl-2 to the IgH enhancer results in inappropriately high levels of bcl-2 gene expression in malignant B lymphocytes.

The Bcl-2 protein is an intracellular integral membrane protein having a molecular mass of about 26 kiloDaltons (kDa). Bcl-2 is present primarily in the nuclear envelope, parts of the endoplasmic reticulum and outer mitochondrial membranes. Bcl-2 likely blocks a distal step in an evolutionarily conserved programmed cell death pathway, thereby contributing to the expansion of a population of tumor cells by promoting cell survival (Reed, *J. Cell Biol.* 124: 1–6 (1994)). Although first identified in lymphomas having t(14;18) translocations, deregulated expression of bcl-2 is not restricted to these tumor cells. High levels of Bcl-2 protein expression and aberrant patterns of Bcl-2 protein production have been observed in a variety of solid tumors, including adenocarcinomas of the prostate and colon, squamous carcinomas of the lung, neuroblastomas and nasopharyngeal carcinomas.

Bcl-2 is expressed in many normal adult tissues, including thymus, lymph nodes, brain, epidermis and intestine. In many cases, the in vivo pattern of Bcl-2 expression in these tissues is consistent with the known role for Bcl-2 as a blocker of cell death. For example, Bcl-2 typically is expressed in self-renewing stem cells or long-lived populations of cells but not in cells that are prone to apoptotic cell death (Hockenberry et al., *Proc. Natl. Acad. Sci., USA* 88: 6961–6965 (1991)).

Expression of Bcl-2 is developmentally regulated and generally is expressed more widely in fetal as compared to adult tissues (LeBrun et al., *Am. J. Pathol.* 142: 743–753 (1993)). In addition, various stimuli, including, for example, lymphokines such as interleukin-2 (IL-2), IL-6 and transforming growth factor-β, some viral proteins such as LMP-2 from Epstein Barr virus, retinoids and phorbol esters can increase or decrease the relative levels of bcl-2 mRNA and Bcl-2 protein primarily by affecting the regulation of bcl-2 gene transcription (Reed et al., *Oncogene Res.* 4: 271–282 (1989)).

Various elements involved in regulating bcl-2 gene expression have been described. The human bcl-2 gene contains two distinct promotor regions, P1 and P2 (Sato et al., *EMBO J.* 7: 123–131 (1988)). The principal promotor region, P1, is in a region containing several GC boxes, which can bind the transcription factor Sp1. The P1 promotor is located approximately 1.7 kilobase pairs (kbp) upstream of the bcl-2 open reading frame and expression from P1 results in a bcl-2 mRNA containing a long 5'-UTR. A second potential promotor, P2, is located approximately 80 bp upstream of the coding region. Fewer than 5% of all transcripts initiate from P2 (Sato et al., supra, 1988).

Expression of the bcl-2 gene is regulated, in part, by a negative regulatory element (NRE) located in the 5'-UTR of the bcl-2 gene. The bcl-2 NRE contains two functionally separable cis-acting inhibitory elements, including a p53-dependent negative response element (Miyashita et al., *Canc. Res.* 54: 3131–3135 (1994a), which is incorporated herein by reference). The p53-dependent element requires the p53 tumor suppressor protein for activity and functions in an orientation-independent and position-independent manner to down-regulate expression of heterologous reporter gene constructs. Thus, the p53-dependent element, which functions equally well in either a sense or antisense orientation and whether placed between or upstream or downstream of the promotor and reporter gene, has the properties of a transcriptional silencer.

The p53 tumor suppressor protein down-regulates bcl-2 gene expression in some cells in vitro, suggesting that failure of a cell to express a normal p53 protein can lead to aberrant regulation of bcl-2 gene expression in cancer cells (Miyashita et al., *Oncogene* 9: 1799–1805 (1994b), which is incorporated herein by reference). However, loss of p53-dependent repression of the bcl-2 gene does not account for the altered bcl-2 gene expression observed in all human tumors having this defect. For example, in some cancers such as adenocarcinoma of the colon, deregulation of bcl-2 gene expression occurs prior to the loss of p53.

Expression of wild-type p53 in some p53-deficient tumor cell lines results in spontaneous cell death (see, for example, Yonish-Rouach et al., supra, 1991; Shaw et al., *Proc. Natl. Acad. Sci., USA* 89: 4496–4499 (1992)). However, restoration of p53 activity in other p53-deficient tumor cell lines, while not sufficient to trigger apoptosis, can render cells relatively more sensitive to induction of apoptosis by radiation and DNA-damaging chemotherapeutic drugs (see, for example, Fisher, *Cell* 539–542 (1994)).

Analysis of tissues from p53-deficient transgenic mice (p53 "knock-out" mice) demonstrated that Bcl-2 levels were elevated only in a few tissues such as prostate and lymphatic organs (Miyashita et al., supra, 1994b). Moreover, while the level of bcl-2 gene expression was increased, the patterns of Bcl-2 protein production remained generally unaltered and ectopic expression of Bcl-2 in tissues such as liver, which do not normally express this protein, was not observed. These results indicate that elements other than a p53 responsive element, alone, are involved in regulating expression of the bcl-2 gene and that other cellular factors such as tissue-specific factors can influence the extent to which p53 are required for regulating the expression of genes involved in cell death.

Expression of bcl-2 gene expression also is regulated, in part, by a p53-independent mechanism conferred by the negative regulatory element (NRE) present between positions -279 to -85, relative to the translation start site of the bcl-2 gene (Young and Korsmeyer, *Mol. Cell. Biol.* 13: 3686–3697 (1993), which is incorporated herein by reference). The bcl-2 NRE can inhibit expression from the homologous bcl-2 gene P1 promotor as well as from heterologous promotors such as the CMV immediate-early region promotor and the SV40 early-region promotor. However, various portions of the NRE appeared to have different activities and the critical nucleotide sequences were not identified.

The present invention provides a BIE, which is a nucleotide sequence that corresponds to a portion of the NRE, including positions -124 to -114, located in the 5'-UTR of the human bcl-2 gene. As disclosed herein, a BIE acts in a position-dependent and orientation-dependent manner to inhibit expression of a nucleic acid molecule such as a reporter gene from the homologous bcl-2 P1 promotor and from various heterologous promotors (see Example I). A BIE of the invention is exemplified by BIE-1, which is an 11 bp nucleotide sequence corresponding to position -124 to -114 of the human bcl-2 gene (SEQ ID NO: 1), and by sequences that correspond to BIE-1, including, for example, the sequences shown as SEQ ID NOS: 3 and 5 to 7.

The invention also provides a BIE binding factor (BBF), which is a cellular factor that can bind specifically to a BIE. The binding of a BBF to a BIE can regulate the expression of a nucleic acid sequence linked to the BIE. As disclosed herein, a BBF can be identified by using a BIE as a probe in a gel shift assay or by screening a cDNA expression library with a BIE probe (see Example II).

A BBF of the invention is exemplified by a BIE-1 binding factor (BBF-A), which is a cellular factor that is present in various different cell lines and that binds specifically to BIE-1 (SEQ ID NO: 1). However, it is recognized that, in some cases, the methods disclosed herein do not distinguish whether one or more than one cellular factor is present or whether cellular factor(s) detected in different tissues are the same factor. For example, a complex formed in a gel shift assay can contain one or more proteins bound to a BIE-1 probe. Thus, while reference is made, for example, to the presence of BBF-A in the complex, it should be recognized that one or more proteins can be present in the complex.

Similarly, different cell types can contain the same or different BBF proteins and the same cell can contain more than one type of BBF. For example, the BBF protein(s) detected in the tumor cell lines examined (see Example II.E.) can be the same protein as shown in FIG. 7 (SEQ ID NO: 9), which is expressed in various cell types, or can be different proteins, each of which is expressed in a tissue-specific manner. It follows that the nucleotide sequence shown in FIG. 7 (SEQ ID NO: 8) does not necessarily encode, for example, the protein(s) present in the complex shown in FIG. 6. Nevertheless, for convenience of discussion, the term "BBF" is used herein to refer to a protein that can specifically associate with a BIE-1, including the polypeptide portion of the protein shown in FIG. 7 (SEQ ID NO: 9), which is termed BBF-A.

Analogous to various well known gene regulatory systems, a BIE can represent a gene regulatory element and a BBF can represent a protein that modulates the level of expression of a nucleic acid molecule such as the bcl-2 gene by virtue of its association with the BIE. Thus, the binding of BBF-A to BIE-1 can regulate the level of bcl-2 gene expression in a cell, which, in turn, can modulate apoptosis of the cell.

Double-stranded DNA oligonucleotides containing the BIE-1 sequence specifically bound a BBF-A present in nuclear extracts from a variety of human tumor cell lines, including cell lines derived from lymphoid, hemopoietic, fibroblast, epithelial and neuronal cell tumors (see Example II). Mutation analysis of BIE-1 provided a means to identify novel BIE sequences (SEQ ID NOS: 3 and 5–7), which correspond to the sequence of BIE-1 (SEQ ID NO: 1), and demonstrated that the inhibition of CAT activity correlated with the ability of the mutant sequences to compete with wild-type BIE-1 for binding to BBF-A in vitro. Gel shift and UV-crosslinking experiments also demonstrated that a BBF-A is present in HeLa cell nuclear extracts and binds specifically to the BIE-1 sequence (see Example II).

When $^{32}$P-labelled BIE-1 was used as a probe to screen a western blot (south-western blot analysis) prepared using HeLa cell protein extract, the probe specifically bound a protein having an apparent molecular mass of about 47 kDa (see FIG. 6). A nucleic acid encoding BBF-A was obtained by screening a cDNA expression library prepared in the lambda EXlox vector with a BIE-1 probe. Thus, the present invention provides a nucleic acid molecule (SEQ ID NO: 8) encoding a polypeptide portion of BBF-A (SEQ ID NO: 9; see FIG. 7).

As disclosed in Example II.D., a cDNA expression library was prepared from HeLa cell RNA and screened using a probe containing tandem repeats of BIE-1 (SEQ ID NO: 1) to identify a cDNA encoding BBF-A (SEQ ID NO: 8; FIG. 7). Following several rounds of screening, one positive clone was identified. The polypeptide encoded by the cloned cDNA was expressed in vitro and specifically bound a BIE-1 probe. Thus, the present invention provides an active fragment of BBF-A. When used in reference to BBF-A, the term "active fragment" means a polypeptide portion of full length BBF-A, provided the polypeptide portion can bind a nucleotide sequence corresponding to BIE-1 (SEQ ID NO: 1).

The nucleotide sequence of the isolated BBF-A cDNA (SEQ ID NO: 8) and the deduced amino acid sequence (SEQ ID NO: 9) are highly homologous to the nucleic acid sequence and amino acid sequence for heteronuclear ribonucleoprotein, hnRNP A/B (SEQ ID NOS: 35 and 36, respectively; see FIGS. 8 and 9; see Khan et al., *Fed. Eur. Biochem. Soc.* 290: 159–161 (1991), which is incorporated herein by reference). Heteronuclear ribonucleoproteins bind heteronuclear RNA (hnRNA) and can provide, for example, a proper structure and environment for hnRNA processing and for transport of the processed RNA out of the nucleus. Although hnRNPs also can bind to single stranded DNA and there has been speculation that they regulate gene transcription or mRNA translation, these hypotheses have not been proved (reviewed in Dreyfuss et al., *Ann. Rev. Biochem.* 62: 289–321 (1993)).

Various hnRNP's are known and are classified according to their molecular weights (see Dreyfuss et al., supra, 1993). In particular, the A/B family of hnRNP's have molecular weights of about 34–43 kDa and, in some cases, migrate with an apparent molecular mass of about 45 kDa in SDS-PAGE, which is similar to the apparent molecular mass of 47 kDa for BBF-A as determined by SDS-PAGE. Thus, BBF-A can be a member of the hnRNP A/B family of proteins, which are characterized in containing two RNP-motif RNA-binding domains and a glycine-rich auxiliary domain at the carboxyl terminus (Dreyfuss et al., supra, 1993). The nucleotide sequence encoding BBF-A and, consequently, the amino acid sequence of BBF-A are identical to hnRNP A/B in these regions (see, for example, FIG. 8, consensus sequences 151–168, 268–290, 403–420 and 523–546).

Another protein, the 285 amino acid mouse protein, "CArG" binding factor, is 88% identical to human hnRNP A/B (Khan et al., supra, 1991). CArG binding factor binds to single stranded DNA. CArG binding factor differs from hnRNP A/B in containing a non-homologous region of 37 amino acids starting at residue 26 of hnRNP A/B. In addition, CArG contains a 3 glycine sequence instead of an 8 glycine sequence beginning at residue 256 of hnRNP A/B. The differences in these two regions may contribute to the different binding characteristics of hnRNP A/B and CArG binding factor (Khan et al., supra, 1991).

The present invention also provides antibodies that specifically bind the polypeptide portion of BBF-A shown in FIG. 7 (SEQ ID NO: 9). As used herein, the term "antibody" is used in its broadest sense to include polyclonal and monoclonal antibodies, as well as polypeptide fragments of antibodies that retain a specific binding activity of at least about $1\times10^5 M^{-1}$. Thus, one skilled in the art would know that anti-BBF-A antibody fragments such as Fab, F(ab')$_2$ and Fv fragments can retain specific binding activity for BBF-A and, thus, are included within the definition of an antibody. In addition, the term "antibody" as used herein includes naturally occurring antibodies as well as non-naturally occurring antibodies and fragments thereof that retain binding activity. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246: 1275–1281 (1989), which is incorporated herein by reference.

Particularly useful non-naturally occurring antibodies include chimeric antibodies and humanized antibodies. As used herein, the term "chimeric antibody" means an antibody having a human constant region and a variable region from an organism other than a human. For example, a chimeric antibody useful in the invention can consist of a human IgG constant region and a variable region obtained from a mouse anti-BBF-A antibody. As used herein, the term "humanized antibody" means an antibody having human constant and framework regions and hypervariable regions from an organism other than a human. For example, a humanized antibody useful in the invention can consist of the amino acids that form the hypervariable region of a mouse anti-human BBF-A antibody and the amino acids that form the framework region and constant regions of a human IgG class antibody. Chimeric antibodies and humanized antibodies are particularly useful for administration to a human subject, since the likelihood of an immune response by the subject against the antibody is minimized.

Anti-BBF-A antibodies can be prepared using substantially purified BBF-A or a BBF-A fusion protein as an immunogen. In addition, a peptide fragment of BBF-A can be used as an immunogen. Substantially purified BBF-A or a peptide fragment of BBF-A can be obtained, for example, by expressing the nucleic acid molecule shown as SEQ ID NO: 8 or a portion of that nucleic acid molecule or by well known methods of chemical synthesis. Methods for raising an antibody are routine and described, for example, by Harlow and Lane, *Antibodies: A laboratory manual* (Cold Spring Harbor Laboratory Press, 1988), which is incorporated herein by reference. A form of BBF-A useful as an immunogen can be prepared from natural sources, as described herein, produced recombinantly or chemically synthesized.

In some cases, a protein such as BBF-A may be poorly immunogenic due, for example, to a high degree of conservation of the protein among various species. In addition, a fragment of BBF-A may not be immunogenic. However, a non-immunogenic protein or fragment thereof can be made immunogenic by coupling it to a carrier molecule such bovine serum albumin or keyhole limpet hemocyanin. In addition, various other carrier molecules and methods for coupling a hapten to a carrier molecule are well known in the art (see, for example, Harlow and Lane, supra, 1988).

Polyclonal anti-BBF-A antibodies can be raised in rabbits. In addition, monoclonal antibodies can be obtained using known methods (Harlow and Lane, supra, 1988). Essentially, spleen cells from a BBF-A-immunized animal can be fused to an appropriate myeloma cell line such as SP/02 or P3x653.Ag8 myeloma cells to produce hybridoma cells. Cloned hybridoma cell lines can be screened using labelled BBF-A polypeptide to identify clones that secrete anti-BBF-A monoclonal antibodies. Methods for labelling a polypeptide are well known (see below). Hybridomas that express antibodies having a desirable specificity and affinity can be isolated and utilized as a continuous source of monoclonal anti-BBF-A antibodies. Methods for identifying an anti-BBF-A antibody having an appropriate specificity and affinity and, therefore, useful in the invention also are known in the art and include, for example, enzyme-linked immunosorbent assays, radioimmunoassays and precipitin assays (Harlow and Lane, supra,, 1988; chap. 14).

An anti-BBF-A antibody of the invention can be useful, for example, to purify BBF-A from a sample. For example, anti-BBF-A antibodies can be attached to a solid substrate such as a resin and can be used to affinity purify BBF-A. In addition, an anti-BBF-A antibody can be used to identify the presence of BBF-A in a sample. In this case, the anti-BBF-A antibody can be labelled so as to be detectable. An anti-BBF-A antibody can be detectably labelled using methods well known in the art (see, for example, Harlow and Lane, 1988; chap. 9). For example, an antibody can be labelled with any of various detectable moieties including a radiolabel, an enzyme, biotin or a fluorochrome. Following contact of a labelled antibody with a sample such as a tissue homogenate or a histological section of a tissue, specifically bound labelled antibody can be identified by detecting the particular moiety.

A labelled second antibody also can be used to identify specific binding of an unlabelled anti-BBF-A antibody. A second antibody generally will be specific for the particular class of the first antibody. For example, if an anti-BBF-A antibody is of the IgG class, a second antibody will be an anti-IgG antibody. Such second antibodies are readily available from commercial sources. The second antibody can be labelled using a detectable moiety as described above. When a sample is labelled using a second antibody, the sample is first contacted with a first antibody, then the sample is contacted with the labelled second antibody, which specifically binds to the first antibody and results in a labelled sample.

Cells in a tissue normally have a predetermined lifespan. Intestinal epithelial cells, for example, have a relatively short lifespan and Bcl-2 levels are low in such cells. In contrast, the lifespan of neuronal cells can be very long and Bcl-2 levels generally are high in such cells. Bcl-2 levels generally also are high in tumor cells. The association of a BBF-A with BIE-1 in a cell can regulate the expression of the bcl-2 gene, which can modulate apoptosis in the cell.

Induction or repression of apoptosis in a particular cell type can alter the lifespan of the cell. Since the association of BBF-A with BIE-1 in a cell can regulate the level of bcl-2 gene expression in the cell, a means for altering the association of BBF-A and BIE-1 can allow modulation of apoptosis in a cell. Accordingly, the invention provides screening assays that are useful for identifying an agent that can alter the association of a BBF and a BIE. An agent can be a biological or chemical compound such as a simple or complex organic molecule, peptide, peptido-mimetic, protein or oligonucleotide. An agent that can increase or decrease, for example, the binding of BBF-A to BIE-1 can modulate the expression of Bcl-2 and, consequently, can modulate apoptosis in the cell.

The screening assays described herein are particularly useful in that they can be automated, which allows for high through-put screening of randomly or rationally designed agents in order to identify those agents that effectively alter the association of a BBF and a BIE (see Example III). Such effective agents can be useful for modulating the level of expression of gene such as bcl-2, which is involved in regulating apoptosis in a cell.

When used in reference to the association of a BIE and a BBF, the term "effective agent" means an agent that alters the association of the BBF and the BIE or otherwise modulates the level of expression of a nucleic acid sequence linked to the BIE. An effective agent can be identified by detecting an altered association of a BIE and a BBF or by detecting an increased or decreased level of expression of a nucleic acid sequence linked to a BIE (see Example III). In particular, an effective agent can be useful for modulating the expression of the bcl-2 gene, which is linked to BIE-1.

A peptide portion of the polypeptide shown as SEQ ID NO: 9 can be an effective agent. For example, the peptide can bind a BIE-1 without altering BIE-1 activity and, by virtue of its binding, can prevent the association of an active BBF-A with the BIE-1. The methods disclosed herein can be used to identify a peptide portion of BBF-A that can be an effective agent. Such effective agent BBF-A peptides should be at least about five amino acids in length and can be identified, for example, first by screening a peptide library (see, for example, Ladner et al., U.S. Pat. No. 5,223,409, which is incorporated herein by reference) to identify peptides that can bind BIE-1, then by performing a screening assay as disclosed herein to identify a BIE-1-binding peptide that does not alter BIE-1 activity.

An effective agent can be identified by its ability to modulate the expression of a nucleic acid molecule linked to a BIE. As used herein, the term "modulate" means increase or decrease. Thus, an effective agent can increase or decrease the level of expression of a nucleic acid sequence. For example, an effective agent can alter the association of BIE-1 and BBF-A in a cell, which can modulate the expression of the bcl-2 gene in the cell and can modulate apoptosis in the cell.

When used in reference to a BIE and a BBF, the term "associate" or "association" means that the BBF and the BIE can bind to each other relatively specifically to form a bound complex. In particular, the association of a BBF and a BIE is sufficiently specific such that the bound complex can form in vivo in a cell or in vitro under suitable conditions (see Example II). As a consequence of modulated bcl-2 gene expression, the progression of apoptosis in the cell can be increased or decreased. In general, an effective agent that can down-regulate bcl-2 gene expression in a cell can increase apoptosis in the cell, whereas an effective agent that can up-regulate bcl-2 expression in a cell can decrease apoptosis in the cell.

When used in reference to a BBF and a BIE, the term "alter the association" means that the ability of the BBF and the BIE to bind each other is increased or is decreased due to the presence of an effective agent as compared to the level of binding in the absence of the agent. As a result of an altered association of a BBF and a BIE in a cell, expression of a gene linked to the BIE can be increased or decreased. For example, an effective agent that can alter the association of BBF-A with BIE-1 can modulate the level of expression of the bcl-2 gene and can modulate apoptosis in a cell.

An effective agent can act by interfering with the ability of a BBF to associate with a BIE or by causing the dissociation of a BBF from a BIE. The binding of a BBF to a BIE can be related to the level of expression of a nucleic acid molecule linked to the BIE. For example, binding of BBF-A to BIE-1, which is linked to the bcl-2 gene, can regulate the expression of the bcl-2 gene in a cell. An effective agent, which can alter the association of a BBF-A to BIE-1, can modulate apoptosis in a cell. Thus, the identification of an effective agent that alters the association of a BBF with a BIE can provide a means to increase or decrease apoptosis in a cell by contacting the cell with the effective agent.

Various diseases such as cancer, stroke, Alzheimer's disease, ataxia telangiectasia, Bloom's syndrome and progeria are characterized, in part, by aberrant regulation of apoptosis. The identification of an agent that can modulate bcl-2 gene expression and apoptosis can provide a means for treating such diseases. For example, in some cases, tumor development is characterized, in part, by high levels of Bcl-2 expression (Tsujimoto and Croce, *Proc. Natl. Acad. Sci., USA* 83: 5214–5218 (1986)) and by decreased rates of cell death (Symonds et al., *Cell* 78: 703–711 (1994)). Furthermore, the relative insensitivity of tumor cells to induction of apoptosis by chemotherapeutic drugs and radiation can be due to high levels of Bcl-2 expression. The ability to modulate the levels of bcl-2 gene expression in a cell can be useful, for example, to increase apoptosis in tumor cells or to render a cancer cell more susceptible to chemotherapeutic agents.

In contrast to cancer, other diseases such as stroke are characterized by abnormally high levels of cell death due to necrosis and apoptosis. In stroke, ischemia and oxygen deprivation leads to necrotic cell death. Subsequent destruction of the necrotic neuronal cells results in the release of agents such as glutamate, which can induce apoptosis in surrounding cells presumably, in part, by allowing intracellular levels of active oxygen species to increase (Behl et al., *Biochem. Biophys. Res. Comm.* 197: 949–956 (1993), which is incorporated herein by reference). Increasing the level of Bcl-2 protein in neuronal cells exposed to glutamate or to agents that induce high intracellular active oxygen concentrations greatly increases cell survival (Behl et al., 1993; Kane et al., 1993).

Alzheimer's disease, ataxia telangiectasia, Bloom's syndrome and progeria also are characterized, in part, by exhibiting abnormally high levels of cell death. Cells in patients having these diseases are characterized by an accumulation of DNA damage due, for example, to oxidative damage or to defects in DNA repair. Cells from ataxia telangiectasia patients, for example, are highly susceptible to UV- and X-radiation, which damages DNA in the cells and induces apoptosis. Increased expression of Bcl-2 in the cells of such patients can be useful for decreasing apoptosis of these cells and, therefore, can improve the patient's quality of life.

An effective agent can be useful, for example, to increase apoptosis in a cell such as a cancer cell, which is characterized, in part, by having a decreased apoptosis as compared to its normal cell counterpart. An effective agent also can be useful, for example, to decrease apoptosis in a cell such as a T lymphocyte in a subject having a viral disease such as acquired immunodeficiency syndrome, which is characterized by an increased apoptosis in an infected T cell as compared to a normal T cell. Thus, an effective agent can be useful as a medicament for altering apoptosis in a subject having a pathology characterized by increased or decreased apoptosis. In addition, an effective agent can be used, for example, to decrease apoptosis and, therefore, increase the survival time of a cell such as a hybridoma cell in culture. The use of an effective agent to prolong the survival of a cell in vitro can significantly improve bioproduction yields in industrial tissue culture applications.

A peptide or polypeptide portion of a BBF can be an effective agent, which can bind to a BIE, thereby decreasing the association of an intact BBF and a BIE in a cell by competing for binding to the BIE. For example, a peptide portion of BBF-A (SEQ ID NO: 9) that can bind to BIE-1 (SEQ ID NO: 1) as determined using a gel shift assay but that does not alter the level of transcription of a gene linked to the BIE-1 as determined using a CAT assay can be used as an effective agent that competes with BBF-A for binding to BIE-1 in a cell. A non-naturally occurring peptido-mimetic also can be useful as an effective agent. Such a peptido-mimetic can include, for example, a peptoid, which is peptide-like sequence containing N-substituted glycines, or an oligocarbamate. A peptido-mimetic can be particularly useful as an effective agent due, for example, to having an increased stability to enzymatic degradation in vivo.

The ability to manipulate the regulatory elements and associated cellular factors involved in the regulation of cell death, including the regulation of cell death in various diseases, and the availability of a variety of cell types from patients having such diseases allows for the identification of agents that can be used to effectively treat patients having these diseases. Thus, the present invention provides screening assays useful for identifying an effective agent (see Example III).

The screening assays described in Example III were used to identify and characterize a BIE of the invention and provide simple and direct methods to identify an effective agent. The gel shift assay is particularly useful because it does not require the use of living cells. Thus, the gel shift assay can be used as a primary method of screening for an effective agent, which can increase or decrease apoptosis in a cell.

In addition to being suitable for developing high throughput assays for screening agents, the assays provide the additional advantage of allowing the identification of agents that effectively regulate the expression of a gene linked to a BIE. Any of several different reporter genes can be used to detect regulation by an effective agent. As used herein, the term "reporter gene" means a gene that encodes a gene product that can be identified using simple, inexpensive methods. As described, below, the chloramphenicol acetyltransferase (CAT) reporter gene can be used to determine the level of transcriptional activity of a nucleic acid molecule linked to a BIE (see Example I). Other reporter genes such as luciferase also can be used in the disclosed assays. Such reporter genes are well known in the art and described, for example, by Sambrook et al., supra, 1989.

Agents that effectively decrease apoptosis are particularly useful for treating a patient having a disease characterized by abnormally high levels of cell death. The effective agent can be administered to the patient, with the route of administration depending on the location of the diseased cells or tissue. For example, a patient with a neurodegenerative disorder, viral encephalitis, stroke, spinal cord injury or hereditary disorders that involve neuronal cell death such as ataxia telangiectasia can be treated by intrathecal administration of an agent. In contrast, it may be advantageous to administer an effective agent intravenously to a cancer patient with metastatic disease. These and other methods of administration are well known in the art and are selected based on the requirements for a particular patient.

The following examples are intended to illustrate but not limit the present invention.

EXAMPLE I

The bcl-2 Gene Inhibitory Element

This example describes the methods for identifying and characterizing various bcl-2 gene inhibitory elements (BIE), including BIE-1.

A. Plasmid constructions

The plasmid p18-21H, which contains a 7.8 kbp Hind III fragment represent the bcl-2 gene promotor region and first exon, (Tsujimoto et al., Proc. Natl. Acad. Sci., USA 84: 1329–1331 (1987), which is incorporated herein by reference) was subjected to PCR amplification using Pfu polymerase as recommended by the manufacturer (Stratagene, Inc.; San Diego, Calif.). PCR amplification produced several fragments that correspond to portions of the NRE located in the 5'-UTR of the human bcl-2 gene. PCR products are designated as "full length" NRE (positions −274 to −84; see FIG. 1; SEQ ID NO: 2) or fragments #1 (positions −274 to −200; #2 (positions −140 to −84); #3 (positions −274 to −140); or #4 (positions −200 to −84) of the human bcl-2 gene 5'-UTR.

Three forward primers, TM12 (5'-GCGAAGCTTGTAGACTG ATATTAAC-3'; SEQ ID NO: 10), MYHO2-2 (5'-GCGAAGCTTAAAATTTCC TGCATCTCAT-3'; SEQ ID NO: 11) and MYHO2-4 (5'-GCGAAGCTTAAGA CACCCCCTCGTCCAA; SEQ ID NO: 12); and three reverse primers, TM13 (5'-GCGAAGCTTATAATCCAGCTATTTT-3'; SEQ ID NO: 13), MYHO2-3 (5'-GCGAAGCTTTATTCCAATTCCTTTCGGA-3'; SEQ ID NO: 14) and MYHO2-1 (5'-GCGAAGCTTCAATCACGCGGAACACTTG-3'; SEQ ID NO: 15), each of which contained an internal Hind III site (underlined), were used for PCR.

Primers were used in the following combinations: TM12 and TM13 to produce the full length NRE; TM12 and MYHO2-3 to produce fragment #1; MYHO2-4 and TM13 to produce fragment #2; TM 12 and MYHO201 to produce fragment #3; and MYHO2-2 and TM13 to produce fragment #4. The resulting PCR products were digested with Hind III and subcloned into pUCSV3CAT, which contains the SV40 early-region promotor upstream of a unique Hind III site and a CAT reporter gene downstream of the cloning site (Fukamizu et al., Biomed. Biochem. Acta 50: 4–6 (1991), which is incorporated herein by reference).

Oligodeoxynucleotides corresponding to shorter regions of the bcl-2 NRE, including the 11 bp BIE-1 sequence or various mutants thereof, also were synthesized with Hind III compatible ends (see FIG. 5; SEQ ID NOS: 1 and 3 to 7). For CAT assays, these oligonucleotides, which corresponded to positions −121 to −107 (5'-agctGAATGCAAAG CACAT-3'/5'-agctATGTGCTTTGCATTC-3'; SEQ ID NOS: 16 and 17); −118 to −107 (5'-agcTGCAAAGCACAT-3'/5'-agctATGTGTTTGC-3'; SEQ ID NOS: 18 and 19); −115 to −107 (5'-agctAAAGCACAT-3'/5'-agctATGTGCTTT-3'; SEQ ID NOS: 20 and 21); −124 to −117 (5'-agctCAAGAATG-3'/5'-agctCATTCTTG-3'; SEQ ID NOS: 22 and 23) were annealed and subcloned into the Hind III site of either pUCSV3CAT or pCEP-CAT, which contains the CMV immediate-early region promotor linked to the CAT reporter gene. In addition, the annealed oligonucleotides were used as competitor DNA in gel shift assays (see Example II). In the gel shift assay, double-stranded DNA corresponding to an Egr-1 binding site (upper case) (5'-gatctCGCGGGGGCGaggggg gatc-3'; SEQ ID NO: 24) was used as an irrelevant competitor.

To construct pCEP-CAT, the 1.6 kb BamHI/HindIII fragment, which contains the CAT reporter gene, was isolated from pUCSV0CAT. pUCSV0CAT was made by deleting the SV40 early-region promotor from pUCSV3CAT. The 1.6 kb fragment from pUCSV0CAT was inserted between the BamHI and Hind III sites of pCEP4 (Invitrogen) to produce pCEP-CAT.

In some cases, the NRE or the synthetic oligodeoxynucleotides were subcloned upstream or downstream of the SV40-CAT transcriptional unit in pUCSV3CAT. The unique Hind III site in pUCSV3CAT was removed by cleaving the plasmid with Hind III, filling in the overhangs using the Klenow fragment of DNA polymerase and ligating the blunt ends. Appropriate linkers were used to generate new Hind III sites at either the BamHI site, which is located downstream of the CAT gene, or at the Bgl II site, which is located upstream of the SV40 promotor, as described by Miyashita et al., supra, 1994a.

To construct P1-CAT, an SstII/SstI fragment of the human bcl-2 gene, which contains positions −1649 to −1295, including the P1 promotor region, was subcloned into pBluescript SK(-II) (Stratagene) to produce pMYH74-81. Plasmid pUCSV0CAT was cut with Sst I and Bam HI, then bluntended and ligated to destroy the unique Sst I and Kpn I sites and generate the plasmid pMYH74-77. The appropriate linkers were used to convert the Hind III and Bgl II sites in pMYH74-77 to Sst I and Kpn I sites, respectively, to generate pMYH-201. Finally, the SstI/KpnI fragment of pMYH74-81, which contains the human bcl-2 gene P1 promotor, was inserted into pMYH-201 to produce P1-CAT. Oligodeoxynucleotides corresponding to positions −124 to −114 of the bcl-2 gene were synthesized with Sst I compatible ends, annealed and cloned into the Sst I site of P1-CAT. Proper construction of all plasmids was confirmed by DNA sequencing.

B. Identification of BIE-1

Transient transfection CAT assays were used to identify and characterize the BIE-1 present in the NRE located in the 5'-UTR of the human bcl-2 gene. For transfection, approximately 2×10⁵ HeLa cells were cultured for 12–24 hr in 60 mm culture dishes in Dulbecco's modified Eagle's medium (DMEM) containing 10% (v:v) fetal calf serum (FCS), 1 mM L-glutamine, 100 U/ml penicillin G and 100 µg/ml streptomycin. Three µg reporter gene plasmid, 1 µg pCMV-β-gal (MacGregor and Caskey, *Nucl. Acids Res.* 17: 2365 (1989), which is incorporated herein by reference) and 20 µg of Lipofectin™ (GIBCO\BRL; Gaithersburg, Md.) in 3.0 ml of Opti-MEM1™ serum-free medium (GIBCO; Grand Island, N.Y.) was added to each plate for 3 hr. Three ml DMEM containing 20% FCS then was added and, after 48 hr, cells were harvested using a rubber policeman and washed 3× with phosphate-buffered saline (PBS; 136 mM NaCl, 2.7 mM KCl, 10 mM Na₂HPO₄, 1.8 mM KH₂PO₄, pH 7.4).

Cells were collected by centrifugation at about 1000×g, then the cell pellets were resuspended in 100 µl ice cold 0.25M Tris-HCl (pH 7.8) and subjected to 3 freeze-thaw cycles. The lysates were centrifuged at 16,000×g for 5 min and the supernatants were collected.

Cos7, NIH 3T3 and Tsu-pr1 cells were maintained in 10% FCS/DMEM, 10% calf serum/DMEM and 10% FCS/RPMI 1640 medium, respectively. 2×10⁵ Cos7 or NIH 3T3 cells were transfected using the method described above for HeLa cells. Alternatively, 2×10⁵ Tsu-pr1 cells were transfected with 7 µg reporter gene plasmid, 1 µg pCMV-β-Gal and 20 µg of Lipofectin™ (GIBCO BRL) for 12–18 hours. CAT assays and β-gal assays were performed as described by Miyashita et al., supra, 1994a.

The full length NRE, in either the sense or the antisense orientation, inhibited the relative level of CAT activity produced from the SV40 promotor-containing reporter gene plasmid in HeLa, Cos7 or NIH 3T3 cells (FIG. 2). Inhibition was consistently greater in the sense as compared to the antisense orientation. Insertion of the full length NRE either upstream of the SV40 promotor or downstream of the CAT reporter gene produced little or no inhibitory activity (FIG. 2). These results demonstrate that the full length NRE functions in a position-dependent, but relatively orientation-independent, manner.

The full length NRE was functionally dissected by examining the activity of 5'- or 3'-truncated mutants of the NRE. Fragments #1 to #4, as described in Example I.A., were inserted between the SV40 promotor and CAT reporter gene in pUCSV3CAT. Fragment #2, which corresponds to positions ⁻140 to ⁻84 of the bcl-2 gene, strongly inhibited the expression of the SV40-CAT reporter gene when inserted in the sense orientation (FIG. 3). In addition, fragment #4, which is a 5'-truncation mutant containing positions ⁻200 to ⁻84, exhibited inhibitory activity, although less so than the ⁻140 to ⁻84 region (fragment #2), when tested in the sense orientation.

Fragment #1, which is a 3'-truncation mutant that corresponds to positions ⁻274 to ⁻200 and, therefore, lacks the ⁻140 to ⁻84 region, retained partial inhibitory activity when tested in the sense orientation. In contrast, fragment #3, which is a 3'-truncation mutant corresponding to positions ⁻274 to ⁻140, had almost no inhibitory activity on CAT reporter gene expression when cloned downstream of the SV40 promotor in the sense orientation (FIG. 3).

Variable levels of inhibitory activity were observed for fragments #1 to #4 when they were subcloned in the antisense orientation between the SV40 promotor and the CAT reporter gene. Fragment #4 suppressed CAT production to about one-half of control levels, fragment #3 had little or no inhibitory activity and fragments #1 and #2 had no inhibitory activity (FIG. 3). These results indicate that at least two negative regulatory elements (⁻274 to ⁻200 and ⁻140 to ⁻84) and one positive regulatory element (⁻200 to ⁻140) are present in the ⁻274 to ⁻84 region of the bcl-2 gene. Furthermore, these results identify the nucleotide sequence corresponding to positions ⁻140 to ⁻84 of the bcl-2 gene as a BIE, which inhibits gene expression in a position-dependent and orientation-dependent manner.

The ⁻140 to ⁻84 region of the NRE (fragment #2) was investigated in greater detail. Fragment #2 exhibited the strongest inhibitory effect on the SV40-CAT reporter gene construct. In the presence of fragment #2, CAT activity was inhibited by about 76% (+/-6%) as compared to the level of CAT activity in the absence of fragment #2. The inhibitory activity was completely orientation-dependent, as no inhibition was observed when fragment 2 was subcloned between the SV40 promotor and the CAT reporter gene in the reverse (antisense) orientation.

Fragment #2 contains TATAA and CCAAT boxes at positions ⁻88 to ⁻84 and ⁻106 to ⁻102, respectively. In order to determine whether either of these elements were involved in the inhibitory response imparted by fragment #2, a 3'-deletion to position ⁻107 was made. Simultaneously, fragment #2 was truncated from the 5'-end to position ⁻132 bp. The ⁻132 to ⁻107 oligonucleotide (fragment #5) was subcloned between the SV40 promoter and the CAT gene in pUCSV3CAT. As shown in FIG. 3, the inhibitory activity of fragment #5 was comparable to that of fragment #2, which contained the CCAAT and TATAA sequences. These results demonstrate that the 26 bp sequence corresponding to positions ⁻132 to ⁻107 of the human bcl-2 gene is a BIE, which confers strong inhibitory activity on a heterologous reporter gene construct when positioned between the promotor and reporter gene in the sense orientation.

To further delineate the nucleotide sequence of the BIE present in the bcl-2 NRE, additional truncated mutants were examined using the CAT reporter gene assay. Truncation of the ⁻132 to ⁻107 fragment from the 5'-end to position ⁻124 had no effect on the ability of this element to repress expression of the SV40-CAT reporter gene plasmid (FIG. 4A). However, deletion to position ⁻121 resulted in essentially complete loss of inhibitory activity. This result indicates that sequences located between or including ⁻124 and ⁻121 are essential for the cis regulatory activity of the bcl-2 inhibitory element.

Truncations from the 3'-end of the -124 to -107 bp region were examined to further delineate the minimum inhibitory element. Sequences between ⁻114 and ⁻107 were dispensable without affecting the inhibitory activity. In contrast, a 3'-truncation mutant to ⁻117 exhibited only minimal inhibitory activity. These results demonstrate that an 11 bp fragment corresponding to positions ⁻124 to ⁻114 of the human bcl-2 gene confers inhibitory activity when cloned in the sense orientation between an SV40 promoter and CAT reporter gene.

The 11 bp sequence, 5'-CAAGAATGCAA-3' (SEQ ID NO: 1), designated bcl-2 inhibitory element-1 (BIE-1), is active in the sense, but not the antisense, orientation (FIG. 4B). In addition, inhibitory activity is detected only when BIE-1 was present between the SV40 promotor and the CAT gene; no activity was detected when BIE-1 was present either upstream of the SV40 promotor or downstream of the CAT gene (FIG. 4B). Thus, BIE-1 is a position-dependent and orientation-dependent gene regulatory element that reduces or inhibits expression of a nucleic acid molecule to which it is linked.

The mouse bcl-2 gene also contains a long 5'-UTR, which shares ~66% nucleotide sequence homology with its human counterpart (Negrini et al., Cell 49: 455-463 (1987), which is incorporated herein by reference). Comparison of the BIE-1 sequence in the human bcl-2 gene with the corresponding sequence in the mouse and rat bcl-2 genes revealed complete conservation of their nucleotide sequences (not shown). In comparison, the chicken bcl-2 gene contains a T→A transversion at position ⁻122 and a deletion of the C at position ⁻116. However, the A at position ⁻119 was conserved. Thus, the chicken bcl-2 gene shares 88% homology with its human counterpart in the region corresponding to the BIE-1.

C. Characterization of BIE-1

The ability of BIE-1 to regulate the expression of the CAT reporter gene from various promotors was examined. In addition to regulating CAT expression from the SV40 promotor, BIE-1 also can regulate expression from the CMV promotor. Insertion of BIE-1 between the CMV immediate-early region promotor and the CAT reporter gene in pCEP-CAT resulted in inhibition of expression when BIE-1 was present in the sense, but not in the antisense, orientation (FIG. 4C). Thus, BIE-1 can regulate gene expression from various heterologous promotors in a position-dependent and orientation-dependent manner.

BIE-1 also inhibited CAT expression when inserted between the bcl-2 P1 promotor and the CAT reporter gene present in the P1-CAT plasmid. In these experiments, the plasmid constructs were transfected into Tsu-prl cells, which are a human prostate cancer-derived cell line that efficiently expresses CAT constructs containing the bcl-2 P1 promotor (not shown). The presence of BIE-1 strongly inhibited expression from the bcl-2 P1 promotor when present in the sense, but not the antisense, orientation (FIG. 4D). Similar inhibitory activity from the bcl-2 promotor (88-92% inhibition; n=3) was observed in HeLa cells (data not shown). Thus, BIE-1 regulates gene expression from the homologous bcl-2 gene P1 promotor as well as from various heterologous promotors.

The BIE-1 was further characterized by constructing a series of oligonucleotides containing point mutations in the BIE-1 sequence or lacking the cytosine residue at position ⁻124 or the adenine at position ⁻114. These mutated BIE-1 sequences were inserted between the SV40 promotor and the CAT reporter gene in pUCSV3CAT and transfected into HeLa cells to determine CAT activity.

An A→T transversion at the nucleotide corresponding to position ⁻119 in the human bcl-2 gene completely abolished BIE-1 activity in CAT assays (see FIG. 5; ⁻119 A→T). Three other mutants, including ⁻123 A→T, ⁻115 A→T and the ⁻124 C deletion, exhibited similar or only slightly weaker inhibitory activity than the wild-type BIE-1 sequence. The ⁻114 A deletion mutant also conferred inhibitory activity, although somewhat less as compared to the control BIE-1 (see FIG. 5). These results indicate that the adenine at position ⁻119 in the bcl-2 gene BIE-1 is required for BIE-1 activity. Furthermore, these results provide four addition examples of BIE's (SEQ ID NOS: 3 and 5 to 7), which have nucleotide sequences corresponding to BIE-1 (SEQ ID NO: 1).

The effect of the presence of BIE-1 on the stability of mRNA containing the transcribed BIE-1 sequence was examined by northern blot analysis. Total RNA was isolated from cells using RNA-Zol B™ solution (Biotecx Laboratories, Inc.; Houston, Tex.) and quantified by determining the absorption at 260 nm. Equivalent amounts of RNA (15 µg) were separated by electrophoresis in 1.5% agarose gels containing 2% formaldehyde and transferred to Zeta-probe™ nylon membranes (Bio-Rad, Inc.; Hercules, Calif.).

Prehybridization and hybridization reactions were performed at 43° C. in 50% formamide, 1 mM EDTA, 0.12M $Na_2HPO_4$, pH 7.2, 7% SDS, 0.25M NaCl, 1× Denhardt's solution and 100 µg/ml salmon sperm DNA (Sambrook et al., supra, 1989). DNA probes were labelled with $\alpha$-$^{32}$P-dCTP by random hexanucleotide priming. Approximately 1×10⁶ cpm probe/ml hybridization solution was added and hybridization was allowed to proceed overnight at 43° C.

Following hybridization, the filters were washed, sequentially, for 15 min each, in 0.1% SDS containing either 2X SSC, 0.5X SSC or 0.1X SSC at room temperature (RT), followed by 0.1X SSC at 65° C. An NcoI/HindIII fragment of pUCSV3CAT was used as a probe to detect CAT mRNA. A cDNA probe for human glyceraldehyde 3-phosphate dehydrogenase (GAPDH) was synthesized by the reverse transcriptase-PCR method from total RNA of human B cell lymphoma cell line, 380, using 5'-CCACCCATGGCAAATTCCATG GCA-3' (SEQ ID NO: 25) as a forward primer and 5'-TCTAG ACGGCAGGTCAGGTCCACC-3' (SEQ ID NO: 26) as a reverse primer. Relative mRNA levels were measured using an image analyzer (Ambis, Inc.; San Diego, Calif.). CAT mRNA results were normalized relative to either β-gal activity or GAPDH mRNA levels.

Positioning the NRE or a BIE downstream of the SV40 promotor in pUCSV3CAT generates a NRE/CAT or BIE/CAT fusion mRNA, respectively. Since BIE-1 potentially can suppress CAT activity due, for example, to decreasing the rate of mRNA translation, decreasing mRNA stability or decreasing gene transcription, the effects of the NRE and fragment of the NRE on steady-state level of CAT mRNA produced from the pUCSV3CAT plasmid was determined.

HeLa cells were transfected with pUCSV3CAT containing either the full length NRE, the ⁻140 to ⁻84 BIE or the ⁻132 to ⁻107 BIE inserted between the SV40 promotor and CAT reporter gene. Steady state levels of CAT mRNA were measured 48 hr later by northern blotting as described above. When present in the sense orientation, the full length NRE, the ⁻140 to ⁻84 BIE and the ⁻132 to ⁻107 BIE inhibited steady-state CAT mRNA levels by 82%, 68% and 57%, respectively, relative to GAPDH mRNA (not shown). In the antisense orientation, the full length NRE inhibited CAT mRNA steady-state levels by about 47%; the ⁻140 to ⁻84 BIE and the ⁻132 to ⁻107 BIE had little or no effect on steady-state CAT mRNA levels. These results are in good agreement with the CAT activity assay results described previously and indicate that inhibitory activity conferred by a BIE is not due to an effect at the level of translation.

The half-life of mRNA produced from the NRE/CAT and BIE/CAT fusion constructs also was determined using northern blot analysis of cells treated with 4 µg/ml actinomycin-D (Act-D; Sigma Chemical Co.; St. Louis, Mo.). HeLa cells were transfected with pCMV-β-Gal and either pUCSV3CAT or pUCSV3CAT containing the ⁻132 to ⁻107 BIE inserted at the Hind III site. After 48 hr, Act-D was added. Cells were harvested 0, 4, 8, 12 or 24 hr later and RNA was isolated. Northern blot analysis was performed and CAT mRNA levels were normalized relative to β-gal activity.

The initial level of CAT mRNA was lower in HeLa cells that had been transfected with the reporter gene plasmid containing the ⁻132 to ⁻107 BIE than in cells that received the parental CAT reporter plasmid. However, the rate of decline in the BIE/CAT fusion mRNA was the same or somewhat slower than for the control CAT mRNA (not shown). These results indicate that the inhibitory activity of a BIE is not due to an altered rate of CAT mRNA degradation. Thus, BIE-1 activity likely due to an effect at the transcriptional level.

EXAMPLE II

Characterization and Cloning of a BIE-1 Binding Factor

This example demonstrates that the bcl-2 inhibitory element, BIE-1, is specifically bound by a BIE-1 binding factor, designated BBF-A, which is expressed in a variety of mammalian cell types.

A. Gel shift assay

In order to determine whether one or more proteins can bind to BIE-1, gel shift assays were performed using a BIE-1 probe corresponding to position ⁻124 to ⁻114 of the NRE located in the 5'-UTR of the human bcl-2 gene. Nuclear extracts were prepared from HeLa cells according to the method of Dignam et al. (*Nucl. Acids Res.* 11: 1475–1489 (1983), which is incorporated herein by reference). Nuclear extracts from other cell lines were prepared by the method of Lassar et al. (*Cell* 66: 305–315 (1991), which is incorporated herein by reference).

The BIE-1 probe, which consisted of a nucleotide sequence corresponding to positions ⁻124 to ⁻114 of the human bcl-2 gene (upper case) flanked by additional sequences (lower case), was prepared by annealing the oligonucleotides 5'-agctCAAGAATGCA (SEQ ID NO: 27) and 5'-agcTTGCATTCTTG-3' (SEQ ID NO: 28). The overhanging ends of the BIE-1 probe were filled in using the Klenow fragment of DNA polymerase in the presence of α-32P-dCTP. Competitor DNA sequences were prepared as described in Example I.A.

Ten µg nuclear extract protein was incubated at RT for 20 min with 0.4 ng $^{32}$P-labelled BIE-1 in 24 µl binding buffer (25 mM Hepes, pH 7.9, 0.5 mM EDTA, 50 mM KCL, 10% glycerol, 0.5 mM dithiothreitol, 0.5 mM phenylmethylsulfonylfluoride (PMSF), 300 µg/ml bovine serum albumin, 1 µg poly (dI-dC) (Pharmacia)). In some experiments, a 100-fold molar excess of various unlabelled competitor DNA sequences (see FIGS. 4A and 5) was added. Following incubation, protein-BIE-1 bound complexes were detected by electrophoresis in non-denaturing 4% polyacrylamide gels using 0.5X TBE buffer (44.5 mM Tris base, 44.5 mM borate, 1 mM EDTA).

Incubation of the BIE-1 probe with nuclear extract retarded the migration of the labelled probe, indicating that one or more nuclear proteins had bound to the BIE-1 sequence (not shown). Specificity of protein binding was examined by adding various competitor DNA sequences to the binding reaction. Addition of a 100-fold molar excess of unlabelled competitor BIE-1 (SEQ ID NO: 1) inhibited formation of the bound complex by greater than 95% as determined by densitometric analysis, whereas addition of an unrelated Egr-1 binding sequence had essentially no effect on formation of the protein-BIE-1 complex. These results indicate that the altered migration of the BIE-1 probe following incubation with HeLa cell nuclear extract is due to specific protein binding to the BIE-1 sequence.

The ability of various 5'- or 3'-deletion mutants of BIE-1 (see FIG. 4A) to compete with BIE-1 for protein-BIE-1 complex formation also was examined. None of the 5'-deletion mutants inhibited formation of the protein-BIE-1 complex. As described above, these same 5'-deletion mutants lack inhibitory activity in CAT assays (see FIG. 4A). The failure of the ⁻121 to ⁻107 sequence, which contains the octamer binding site, to inhibit protein-BIE-1 complex formation indicates that octamer binding proteins are not involved in the protein-BIE-1 complex. A 3'-deletion mutant (⁻124/⁻117) partially inhibited the formation of protein-BIE-1 complexes (approximately 32% inhibition). This 3'-deletion mutant also had weak inhibitory activity in CAT assays (see FIG. 4A). These results demonstrate that the ability of a portion of the bcl-2 gene NRE to inhibit CAT gene expression is correlated to the ability of the BIE to compete with protein-BIE-1 binding.

To ability of point mutants of BIE-1 to compete with formation of the protein-BIE-1 complex also was examined and compared with the ability of the various point mutants to inhibit CAT activity (see Example I.C.; see, also, FIG. 5 for sequence designations). Consistent with the CAT assay results, the ⁻119 A→T mutant competed poorly for protein binding to BIE-1 (35% mean inhibition; n=3) and the irrelevant Egr-1 oligonucleotide competitor had essentially no effect (6% inhibition; n=3). The remaining BIE-1 mutants efficiently competed with the BIE-1 probe for factor binding, although, in some cases, slightly less effectively than the wild type BIE-1 sequence (not shown). The average inhibition of binding of the point mutants relative to wild type competitor was as follows: ⁻124/⁻115 bp (100%); ⁻123/⁻114 bp (89%); ⁻115 A→T (88%); and ⁻123 A→T (73%) (n=3). These results demonstrate that the adenine residue at position ⁻119 of the bcl-2 gene BIE-1 is required for BIE inhibitory activity and for specific protein binding.

B. DNA-protein UV-crosslinking

A photoreactive $^{32}$P-labelled BIE-1 probe was prepared by annealing an oligonucleotide (5'-agctCAAGAATGC AAgctaagctt-3'; SEQ ID NO: 29), corresponding to positions ⁻124 to ⁻114 of the human bcl-2 gene (upper case letters) flanked by additional sequences (lower case), with a partially complementary oligonucleotide (5'-aagcttagcT-3'; SEQ ID NO: 30). The single-stranded region was filled in using Klenow fragment in the presence of α-32P-dCTP, α-$^{32}$P-dGTP, dATP and equimolar amounts of dTTP and 5-bromo-2'-deoxyuridine 5'-triphosphate (BrdU) (see Wu et al., *Science* 238: 1247–1252 (1987), which is incorporated herein by reference).

Protein-BIE-1 binding reactions were allowed to proceed in the presence or absence of a 100-fold molar excess of an unsubstituted competitor BIE-1 and the protein-BIE-1 complexes were resolved in non-denaturing 4% polyacrylamide gels using 0.5X TBE buffer. Gels were exposed to UV light for 30 min at 4° C. using a Fotodyne transilluminator. Radioactive bands were excised from the gel, eluted in 10 mM Tris (pH 7.4) and 1 mM EDTA overnight at 4° C., ethanol-precipitated using 0.3M Na-acetate (pH 5.5) with 10 µg yeast RNA as a carrier, washed in 70% ethanol, dried and analyzed by 6–20% gradient SDS-PAGE (Messier et al., *Proc. Natl. Acad. Sci., USA* 90: 2685–2689 (1993), which is incorporated herein by reference).

Two protein-BIE-1 complexes were detected and migrated as approximately 41 kDa and 27 kDa bands relative to protein molecular weight markers (not shown). Formation of the 27 kDa protein-BIE-1 complex was inhibited only partially (33%) upon addition of excess unlabelled BIE-1, indicating that the complex contains one or more non-specifically bound proteins. In contrast, formation of the larger complex was substantially inhibited (71%) by the addition of excess, unlabelled BIE-1 and by various DNA sequences that correspond to BIE-1 as described above but not by the addition of the unrelated Egr-1 binding sequence or by a DNA sequence that lacks BIE-1 activity. These results indicate that a cellular factor, designated bcl-2 inhibitory factor-1 (BBF-A), specifically binds BIE-1.

C. South-western blot analysis of a BBF

Protein extracts were prepared from HeLa cells and 25 µl aliquots were subjected to SDS-PAGE and transferred to nitrocellulose filters. The blots were cut into sections representing individual lanes from the original gel and incubated with a $^{32}$P-end-labelled double strand DNA probe containing 3 tandem copies of the BIE-1 sequence (SEQ ID NO: 1) or a mutant BIE-1 sequence. The wild type BIE-1 probe was prepared by annealing the following oligonucleotides: 5'-TCTACAGAATGCAAGCTCAGAATGCAA GCTCAGAATGCAA-3' (SEQ ID NO: 31) and 5'-TCGATTGCATTCTTGAGC TTGCATTCTTGAGCTTGCATTCTTG-3' (SEQ ID NO: 32). The mutant BIE-1 probe was prepared by annealing the following oligonucleotides: 5'-TCTACTGATTGCAAGCTCTGATTGCAAGCTCTGATTG CAA-3' (SEQ ID NO: 33) and 5'-TCGATTGCAATCATGAGCTTGCAATCAT GAGCTTGCAATCATG-3' (SEQ ID NO: 34). The sequences in italics indicate the BIE-1 sequence (SEQ ID NO: 1) and the underlined residues indicate the "T" and "A" substitutions in the mutant BIE-1 probe.

As shown in FIG. 6, the wild type BIE-1 probe bound to a HeLa cell protein having a molecular weight of about 47 kDa (lane 1). Specificity of binding was shown by preincubating the HeLa cell extract with a 200-fold molar excess of various competitor DNA sequences prior to adding the labelled wild type BIE-1 probe. Competition with an unlabelled wild type BIE-1 (SEQ ID NO: 1) sequence inhibited binding of the 47 kDa protein to the tandem copy BIE-1 probe (lane 2), whereas competition with the mutant BIE-1 sequence (lane 3) or an irrelevant nucleotide sequence (lane 4) did not affect binding of the BIE-1 probe to the 47 kDa protein.

The specificity of binding of the binding reaction was confirmed by showing that the 47 kDa protein bound only minimally to the mutant BIE-1 sequence, which contained two nucleotide mismatches in the BIE-1 sequence (not shown). These results demonstrate that a BIE-1 specifically binds to a HeLa cell BBF-A having an apparent molecular mass of about 47 kDa.

D. Cloning of BBF-A cDNA

A lambda EXlox cDNA expression library prepared from HeLa cell RNA was purchased from Novagen, Inc. and screened according to the manufacturer's instructions (see, also, Singh et al., Cell 52: 415–423 (1988), which is incorporated herein by reference). Briefly, the phage library was titered and grown at high density (about $10^5$ pfu/150 mm plate) on agarose plates at 37° C. The phage were transferred to nitrocellulose filters and screened using a $^{32}$P-labelled tandem copy BIE-1 probe described above.

Twenty-four positive plaques were detected following a primary screen of $1.2 \times 10^6$ clones. The positive plaques were collected by coring the region of the plaque and secondary screens were performed at about $2 \times 10^6$ pfu/150 mm plate. One clone remained positive following the secondary screening and was isolated and screened at about 500 pfu/100 mm plate. Well-isolated plaques were recovered to obtain individual phage clones and a cDNA insert containing about 750 nucleotides was isolated. A partial sequence of the cDNA insert (SEQ ID NOS: 8) and the deduced amino acid sequence (SEQ ID NOS: 9) are shown in FIG. 7. The cloned cDNA sequence was compared to nucleic acid sequences entered into GenBank and was homologous to a portion of the nucleic acid sequence encoding heteronuclear ribonucleoprotein hnRNP A/B (FIG. 8; SEQ ID NO: 35; Khan et al., supra, 1991; see, also, FIG. 9, comparing the amino acid sequences of hnRNP A/B and BBF-A).

To confirm that the cDNA encoded a BIE-1 binding protein, south-western blot analysis was performed using the cDNA-encoded protein expressed in vitro. The EXlox phage containing the 750 nucleotide putative BBF-A cDNA was converted to a plasmid by passage through E. coli BM25.8, which contains the P1 cre recombinase and the cDNA was expressed as a T7 phage protein 10 fusion protein by induction with IPTG in E. coli XL-1 Blue™ (Stratagene) according to the manufacturer's instructions. IPTG-induced bacteria were lysed in Laemmli buffer and the lysates were serially diluted in Laemmli buffer and the samples were subjected to SDS-PAGE and transferred to nitrocellulose. As a control, an irrelevant protein, BAG-1, was treated in parallel. The blot was incubated with the $^{32}$P-labelled BIE-1 probe or the labelled mutant BIE-1 probe described in Example II.C.

The BIE-1 probe, but not the mutant BIE-1 probe, bound specifically to the recombinant fusion protein prepared from the EXlox cloned cDNA (not shown). The control BAG-1 protein did not bind to either probe (not shown). These results indicate that the cloned cDNA encodes at least a portion of a BBF protein that specifically associates with BIE-1.

E. BBF-A expression in tumor cell lines

Various tumor cell lines, including human cervical carcinoma (HeLa), monkey kidney (Cos 7), human neuroblastoma (SH-SY5Y), human breast adenocarcinoma (MCF 7), human prostate adenocarcinoma (Tsu-prl), chronic myelogenous leukemia (K562), EBV-immortalized β-lymphoblastoid cells (BJAB), Burkitt B-cell lymphoma (Daudi), pre-B-cell acute lymphocytic leukemia (ALL1), t(14;18)-containing non-Hodgkin's B-cell lymphoma (RS11846) and human T-cell ALL (JURKAT; CEM) cells, were examined using the gel shift assay as described above to determine whether BIE-1 binding factors (BBF-A) are expressed. In addition, the tumor cell lines were examined by immunoblot analysis to determine the level of Bcl-2 protein present.

For immunoblot analysis, cells were washed 3× with ice cold PBS, then approximately $1 \times 10^6$ cells were resuspended in 50 µl ice cold lysis buffer (10 mM Tris-HCl, pH 7.4, 0.15M NaCl, 5 mM EDTA, 1% (v/v) Triton X-100) containing the protease inhibitors (1 mM PMSF, 0.28 U/ml aprotinin, 50 µg/ml leupeptin, 1 mM benzamidine and 0.7 µg/ml pepstatin). The cells were incubated for 30 min on ice, then debris was removed by centrifugation at 16,000×g for 10 min and aliquots of the supernatants containing 30 µg total protein were fractionated by SDS-PAGE using 12% gels (Reed et al., Canc. Res. 51: 6529–6538 (1989), which is incorporated herein by reference).

Following electrophoresis, proteins were transferred to nitrocellulose filters and Bcl-2 protein was detected using a rabbit antiserum specific for amino acids 41 to 54 of the human Bcl-2 protein (Reed et al., supra, 1989) and colorimetric detection assays (Krajewski et al., Amer. J. Pathol. 145: 1323–1333 (1994), which is incorporated herein by reference; Miyashita et al., supra, 1994b). Blots also were incubated with an antiserum specific for $F_1\beta$-ATPase to verify that equal amounts of proteins were loaded in each lane (Krajewski et al., Canc. Res. 53: 4701–4714 (1993), which is incorporated herein by reference).

The highest relative amounts of BBF-A activity were detected in HeLa (a human cervical cancer line), Cos7 (SV40-transformed monkey kidney cell) and Tsu-prl (human prostate adenocarcinoma line) (not shown). These cell lines also were able to efficiently repress expression of CAT reporter gene plasmids containing the BIE-1 sequence (see FIG. 2). HeLa and Tsu-prl cells contained relatively low levels of Bcl-2 protein, indicating that some cell lines show an inverse correlation between the amount of BIE-1 binding activity and bcl-2 gene expression. However, the lowest relative level of BBF-A was detected in the T cell acute lymphocytic leukemia (ALL) line CEM, which contained low levels of Bcl-2 protein. This result confirms that bcl-2 gene expression also can be regulated by a BIE-1-independent mechanism.

Substantial levels of BIE-1 binding activity also were detected in RS11846 cells, which is a B cell lymphoma cell line containing high levels of Bcl-2 protein due to a t(14;18) chromosomal translocation and consequent deregulation of bcl-2 gene expression. This result indicates that a cell can contain mechanisms for overriding the inhibitory effect of a BBF.

The approximate sizes of the shifted BBF-A/BIE-1 complexes were similar for all cell lines examined, except that Jurkat and CEM cells, which both are T cell ALL cell lines, also contained small amounts of slower migrating complexes. This result indicates that additional tissue-specific BBF-A proteins can bind to BIE-1 or that the stoichiometry of a BBF-A/BIE-1 interaction is different in these lymphoid leukemia cells.

EXAMPLE III

Screening Assays for Identifying an Effective Agent that Modulates Expression of a Nucleic Acid Molecule Linked to a BIE This example describes screening assays that are useful for identifying an agent that can modulate the expression of a nucleic acid molecule linked to a BIE. Such an effective agent, which can alter the association, for example, of BBF-A and BIE-1 can be used to modulate the expression of the bcl-2 gene in a cell and, thereby, modulate apoptosis in the cell.

A. Transfection Screening Assays

Transfection of a cell with a plasmid containing a BIE linked to a reporter gene such as CAT is useful for obtaining a cell line that can be used to screen for an agent that effectively modulates the expression of the reporter gene. The cell line can be transfected so as to transiently express the reporter gene or, if desired, to obtain a stably transfected cell line. A stably transfected cell line can be useful for providing relatively standard assay conditions among different investigations. Methods for obtaining a stably transfected cell line are well known in the art and described, for example, by Sambrook et al., supra, 1989, and by Ausubel, supra, 1994. Methods for performing transient transfection assays are described in Example I.

A screening assay using cells transfected to express a reporter gene linked to a BIE can be used to identify an effective agent by measuring the level of expression of the reporter gene. The assay can be performed conveniently in 96 well plates, which allow for the screening of a large number of agents in parallel. Various reporter genes such as a CAT or a luciferase gene can be used in the assay. The use of a reporter gene such as the luciferase gene provides the advantage that, following addition of the agent, the 96 well plates can be automatically scanned by a luminescence detector to identify those agents that modulate the level of expression of the reporter gene.

Modulation of the level of expression of the reporter gene due to an effective agent can be determined by comparison of the level of reporter gene activity in the absence of the agent with the level of activity following contact of the cells containing the BIE-reporter gene construct with an agent. An effective agent can be identified by detecting an altered level of expression of the reporter gene following contact with the agent. Depending on the choice of reporter gene used in the assay, altered expression can be detected, for example, by measuring a change in luminescence due to altered luciferase expression or a change in CAT activity or CAT mRNA levels using methods as disclosed in Example I.

In a transient expression assay, for example, transfection of a population of cells with a BIE-reporter gene construct will produce transient expression of the reporter gene. The level of reporter gene expression in the transfected cells can be determined using the methods disclosed herein or otherwise known in the art. Aliquots of the transfected cell population can be contacted with one or more agents and the level of expression of the reporter gene can be measured following such contact. An effective agent can be identified by detecting an increase or decrease in the level of expression of the reporter gene as compared to the level in cells not contacted with the agent.

An effective agent within the present invention mediates its effect through the BIE, which is linked to the reporter gene. Appropriate controls will confirm that the agent is mediating its effect through the BIE. For example, a control population of cells will be transfected with a reporter gene that is not linked to a BIE. An effective agent, which modulates the expression of the reporter gene linked to a BIE, will not affect the level of expression of a reporter gene that lacks the BIE or contains the BIE in an antisense orientation or in a position other than between the promotor and coding region of the reporter gene.

It is recognized that an effective agent can either increase or decrease expression of a nucleic acid molecule linked to a BIE. Thus, an effective agent that decreases the expression of a nucleic acid molecule linked to a BIE can be useful, for example, to decrease the level of expression of the bcl-2 gene in a cell, which can increase apoptosis in the cell. The ability of such an effective agent to induce apoptosis, for example, in a cancer cell can be determined using the screening assays described in Example III, below. Alternatively, an effective agent can increase the level of expression of a nucleic acid molecule linked to a BIE. Such an effective agent, which can be used to increase the level of expression of the bcl-2 gene in a cell and, thereby, increase the lifespan of the cell, can be useful, for example, to prolong the survival of a cell such as a hybridoma cell in culture.

B. Gel shift screening assays

The gel shift assay as described above provides a simple and efficient method of screening various agents to identify an agent that effectively alters the association of a BBF and a BIE. The method can be automated and, therefore, allows for the rapid screening of a large number of potentially effective agents.

This binding reactions are performed essentially as described in Example II, except that the reactions are performed in 96 well plates and various agents are added to the well as appropriate. Following incubation of the samples can be transferred in parallel to precast gels for separation of the reaction products. An agent that effectively decreases the association of a BIE and a BBF can readily be identified by detecting decreased shifting of the labelled BIE probe. An agent that effectively increases the association of a BIE and a BBF can be identified by determining that an increased amount of an unlabelled specific competitor oligonucleotide is required to decrease the amount of the shifted labelled BIE probe. The amount of bound and unbound BIE can be determined, for example, using laser densitometry of autoradiographs of the gels containing the reaction products.

An agent that effectively alters the association of a BBF and a BIE in a cell can modulate the level of expression of the nucleic acid molecule linked to the BIE. For example, as disclosed in Examples I and II, the inhibitory activity of BIE-1 was correlated to specific association of a BBF with the BIE-1. The ability of an effective agent identified using the gel shift assay to modulate expression of a nucleic acid molecule linked to a BIE can be determined using the assay disclosed in Example III.A. Similarly, the ability of an effective agent identified using the gel shift assay to modulate apoptosis in a cell can be determined using the assay disclosed in Example III.C. below.

C. Apoptosis assays

Effective agents identified using the methods described above can be further selected based on their activity for modulating apoptosis in a cell. The apoptosis screening assay can be used to determine whether an effective agent identified using the assays disclosed above also can modulate apoptosis in a cell such as in a cell obtained from a subject having a pathology characterized, in part, by an altered level of apoptosis.

For this assay, the cells to be tested can be, for example, 1) cells that are obtained from the American Tissue Type Culture and are known to exhibit the characteristics of a cell obtained from a patient having a particular disease such as a cancer or a pathology such as ataxia telangiectasia or 2) a neuronal cell line such as described by Behl et al., *Biochem. Biophys. Res. Comm.* 197: 949–956 (1993), which is incorporated herein by reference, that is exposed, for example, to amyloid beta protein (ABP) or to glutamate and, therefore, is a model for the type of cell death that occurs in Alzheimer's disease or in stroke, respectively. An advantage of using such cells in the apoptosis assay is that these cell lines are adapted for tissue culture. However, the cells to be assayed also can be obtained from a subject to be treated and can be adapted for short term culture.

The apoptosis assay can be performed by contacting aliquots of the cells to be tested with an agent such as an effective agent identified using the assays described above, then determining the length of time the cells survive in culture. An agent that effectively modulates apoptosis in a cell can be identified by its ability to increase or decrease the lifespan of the cell as compared to lifespan of cells that are not contacted with an agent. It should be recognized that effective agents as described herein act by altering the activity of a BIE and that agents that induce apoptosis through other mechanisms are not considered effective agents as that term is used herein.

Although the invention has been described with reference to the disclosed examples, it should be understood that various modifications can be made without departing from the spirit of the invention. Accordingly, the invention is limited only by the following claims.

We claim:

1. An in vitro method for identifying an effective agent that alters the association of a Bcl-2 inhibitory element (BIE) and a BIE binding factor (BBF), comprising the steps of:
  a. incubating in solution or in cultured cells the BBF and the BIE, under conditions that allow said BBF and said BIE to associate, with an agent suspected of being able to alter the association of said BBF and said BIE; and
  b. detecting the altered association of said BBF and said BIE, wherein said altered association identifies an effective agent.

2. The method of claim 1, wherein said incubating step is preformed in a cell-free solution and said incubating is in solution.

3. The method of claim 1, wherein said incubating step is preformed in cells in culture and said incubating is in said cells.

4. The method of claim 1, wherein said BIE is BIE-1 (SEQ ID NO: 1).

5. The method of claim 1, wherein said BIE is selected from the group consisting of:
  CTAGAATGCAA (SEQ ID NO: 3);
  CAAGAATGCTA (SEQ ID NO: 5);
  AAGAATGCAA (SEQ ID NO: 6); and
  CAAGAATGCA (SEQ ID NO: 7).

6. The method of claim 1, wherein said BBF is BBF-A, comprising the amino acid sequence shown in FIG. 7 (SEQ ID NO: 9).

7. The method of claim 1, wherein said effective agent is a peptide portion of the amino acid sequence shown in FIG. 7 (SEQ ID NO: 9).

8. An in vitro method for identifying an effective agent that modulates Bcl-2 inhibitory element (BIE) dependent expression of a nucleotide sequence molecule, comprising the steps of:

a. incubating in solution or in cultured cells a nucleic acid molecule, said nucleic acid molecule comprising, in order and operably linked in a sense orientation, a promotor, the BIE and said nucleotide sequence, under conditions that allow the expression of said nucleotide sequence, with an agent suspected of being able to modulate the expression of said nucleotide sequence due to an effect on said BIE; and b. detecting modulated expression of said nucleotide sequence, wherein said modulated expression identifies an effective agent.

9. The method of claim 8, wherein said incubating step is preformed in a cell-free solution and said incubating is in solution.

10. The method of claim 8, wherein said incubating step is preformed in cells in culture and said incubating is in said cells.

11. The method of claim 8, wherein said nucleic acid molecule is bcl-2.

12. The method of claim 8, wherein said BIE is BIE-1 (SEQ ID NO: 1).

13. The method of claim 8, wherein said BIE is selected from the group consisting of:

CTAGAATGCAA (SEQ ID NO: 3);

CAAGAATGCTA (SEQ ID NO: 5);

AAGAATGCAA (SEQ ID NO: 6); and

CAAGAATGCA (SEQ ID NO: 7).

14. The method of claim 8, wherein said effective agent is BIE binding factor A, comprising the amino acid sequence shown in FIG. 7 (SEQ ID NO: 9).

15. The method of claim 8, wherein said effective agent is a peptide portion of the amino acid sequence shown in FIG. 7 (SEQ ID NO: 9).

* * * * *

UNITED STATES PATENT AND TRADEMARK OFFICE
CERTIFICATE OF CORRECTION

PATENT NO. : 5,643,727  
DATED : Jul. 1, 1997  
INVENTOR(S) : Reed et al.

Page 1 of 2

It is certified that error appears in the above-identified patent and that said Letters Patent is hereby corrected as shown below:

In column 4, lines 39-40, please insert --as-- after "shown" and before "SEQ ID".

In column 11, line 19, please delete "such" and replace therefor with --such as--.

In column 14, line 43, please delete "is peptide-like" and replace therefor with --is a peptide-like--.

In column 15, line 52, please delete "GCGAAGCTTGTAGACTG ATATTAAC-3';" and replace therefor with --GCGAAGCTTGTAGACTGATATTAAC-3';--.

In column 15, line 53, please delete "(5'-GCGAAGCTTAAAATTTCC" and replace therefor with --(5'-GCGAAGCTTAAAATTTCC--.

In column 15, line 55, please delete "GCGAAGCTTAAGA CACCCCCTCGTCCAA;" and replace therefor with --GCGAAGCTTAAGACACCCCCTCGTCCAA;--.

In column 15, line 57, please delete "GCGAAGCTTATAATCCAGCTATTTT-3';" and replace therefor with --GCGAAGCTTATAATCCAGCTATTTT-3';--.

UNITED STATES PATENT AND TRADEMARK OFFICE
CERTIFICATE OF CORRECTION

PATENT NO.  : 5,643,727
DATED       : Jul. 1, 1997
INVENTOR(S) : Reed et al.

It is certified that error appears in the above-identified patent and that said Letters Patent is hereby corrected as shown below:

In column 15, line 59, please delete "GCGAAGCTTTATTCCAATTCCTTTCGGA-3';" and replace therefor with --GCG<u>AAGCTT</u>TATTCCAATTCCTTTCGGA-3';--.

In column 15, line 61, please delete "GCGAAGCTTCAATCACGCGGAACACTTG-3';" and replace therefor with --GCG<u>AAGCTT</u>CAATCACGCGGAACACTTG-3';--.

In column 16, line 27, please delete "gatctCGCGGGGGCGagggg gatc-3';" and replace therefor with --gatctCGCGGGGGCGaggggatc-3';--.

Signed and Sealed this

Tenth Day of April, 2001

NICHOLAS P. GODICI

*Attest:*

*Attesting Officer*       *Acting Director of the United States Patent and Trademark Office*